(12) United States Patent
Singh

(10) Patent No.: US 11,337,739 B2
(45) Date of Patent: May 24, 2022

(54) MULTIPLANAR FIXATION PLATE FOR FRACTURE REPAIR

(71) Applicant: GLabs X, LLC, Belmont, CA (US)

(72) Inventor: Anshuman Singh, San Diego, CA (US)

(73) Assignee: GLabs X, LLC, Belmont, CA (US)

( * ) Notice: Subject to any disclaimer, the term of this patent is extended or adjusted under 35 U.S.C. 154(b) by 62 days.

(21) Appl. No.: 16/226,455

(22) Filed: Dec. 19, 2018

(65) Prior Publication Data

US 2019/0183549 A1 Jun. 20, 2019

Related U.S. Application Data

(60) Provisional application No. 62/655,147, filed on Apr. 9, 2018, provisional application No. 62/608,541, filed on Dec. 20, 2017.

(51) Int. Cl.
*A61B 17/80* (2006.01)
*A61B 17/86* (2006.01)

(52) U.S. Cl.
CPC ...... *A61B 17/8061* (2013.01); *A61B 17/8085* (2013.01); *A61B 17/8033* (2013.01); *A61B 17/8057* (2013.01); *A61B 17/86* (2013.01)

(58) Field of Classification Search
CPC .......................... A61B 17/80; A61B 17/8061
See application file for complete search history.

(56) References Cited

U.S. PATENT DOCUMENTS

| | | | |
|---|---|---|---|
| 6,096,040 A | 8/2000 | Esser | |
| D440,311 S | 4/2001 | Michelson | |
| 6,221,073 B1 | 4/2001 | Weiss et al. | |
| 7,137,987 B2 | 11/2006 | Patterson et al. | |
| 7,179,260 B2 | 2/2007 | Gerlach et al. | |
| 7,335,204 B2 | 2/2008 | Tornier | |
| 7,537,604 B2 | 5/2009 | Huebner | |
| 7,635,381 B2 | 12/2009 | Orbay | |
| 7,771,457 B2 | 8/2010 | Kay et al. | |
| D623,744 S | 9/2010 | Strnad et al. | |
| 7,799,061 B2 | 9/2010 | Kay et al. | |
| D631,162 S | 1/2011 | Graham | |
| 7,905,910 B2 | 3/2011 | Gerlach et al. | |
| 7,909,858 B2 | 3/2011 | Gerlach et al. | |
| 7,951,176 B2 | 5/2011 | Grady, Jr. et al. | |
| 7,963,981 B2 | 6/2011 | Binder et al. | |
| 8,100,954 B2 | 1/2012 | Kay et al. | |

(Continued)

FOREIGN PATENT DOCUMENTS

| JP | 2011-019710 | 2/2011 |
|---|---|---|
| JP | 2016-104061 | 6/2016 |

OTHER PUBLICATIONS

Search Report & Written Opinion issued in application No. PCT/US2018/066494 dated Apr. 16, 2019.

(Continued)

*Primary Examiner* — Christopher J Beccia
(74) *Attorney, Agent, or Firm* — Knobbe Martens Olson & Bear LLP

(57) ABSTRACT

Bone surgical plate devices and methods for use in bone fracture surgeries, for example, clavicle fracture surgery. The systems and methods can include a plate device with specific design features including but not limited to differing designs, geometries, and configurations in multiple segments of the device.

21 Claims, 14 Drawing Sheets

(56) References Cited

U.S. PATENT DOCUMENTS

| | | |
|---|---|---|
| 8,105,367 B2 | 1/2012 | Austin et al. |
| 8,118,846 B2 | 2/2012 | Leither et al. |
| 8,172,884 B2 | 5/2012 | Bouman |
| 8,177,822 B2 | 5/2012 | Medoff |
| 8,182,517 B2 | 5/2012 | Sixto, Jr. et al. |
| 8,192,472 B2 | 6/2012 | Sixto, Jr. et al. |
| 8,197,521 B2 | 6/2012 | Sixto, Jr. et al. |
| D663,840 S | 7/2012 | Graham |
| D663,841 S | 7/2012 | Graham |
| D663,842 S | 7/2012 | Graham |
| 8,231,663 B2 | 7/2012 | Kay et al. |
| 8,236,034 B2 | 8/2012 | Binder et al. |
| 8,382,807 B2 | 2/2013 | Austin et al. |
| 8,398,687 B2 | 3/2013 | Vasta et al. |
| 8,398,717 B2 | 3/2013 | Kleinman |
| 8,403,967 B2 | 3/2013 | Orbay |
| 8,591,554 B2 | 11/2013 | Raven, III et al. |
| 8,603,148 B2 | 12/2013 | Raven, III et al. |
| 8,790,378 B2 | 7/2014 | Castaneda et al. |
| 8,852,246 B2 | 10/2014 | Hansson |
| 8,888,824 B2 | 11/2014 | Austin et al. |
| 8,906,075 B2 | 12/2014 | Conley et al. |
| 8,940,028 B2 | 1/2015 | Austin et al. |
| 8,986,353 B2 | 3/2015 | Johnson et al. |
| 8,992,581 B2 | 3/2015 | Austin et al. |
| 9,005,253 B2 | 4/2015 | Appenzeller et al. |
| 9,023,052 B2 | 5/2015 | Lietz et al. |
| 9,066,766 B2 | 6/2015 | Raven, III et al. |
| 9,066,767 B2 | 6/2015 | Buchbinder et al. |
| 9,144,443 B2 | 9/2015 | Leither et al. |
| 9,149,313 B2 | 10/2015 | Strnad et al. |
| 9,220,549 B2 | 12/2015 | Glickel |
| 9,259,251 B2 | 2/2016 | Kay et al. |
| 9,259,252 B2 | 2/2016 | Kay et al. |
| 9,259,253 B2 | 2/2016 | Kay et al. |
| 9,295,506 B2 | 3/2016 | Raven, III et al. |
| 9,301,789 B2 | 4/2016 | Schonhardt et al. |
| 9,326,802 B2 | 5/2016 | Binder et al. |
| D766,437 S | 9/2016 | DaCosta |
| 9,492,213 B2 | 11/2016 | Orbay |
| 9,510,881 B2 | 12/2016 | Castaneda et al. |
| 9,545,278 B2 | 1/2017 | Ducharme et al. |
| 9,572,607 B2 | 2/2017 | Johnson et al. |
| 9,572,609 B2 | 2/2017 | Orbay |
| 9,636,157 B2 | 5/2017 | Medoff |
| 9,649,141 B2 | 5/2017 | Raven, III et al. |
| 9,713,485 B2 * | 7/2017 | Guy .................. A61B 17/8066 |
| 9,717,599 B1 | 8/2017 | Gorelick |
| 9,795,424 B2 | 10/2017 | Austin et al. |
| 9,814,504 B2 | 11/2017 | Ducharme et al. |
| 9,861,409 B1 | 1/2018 | Agee et al. |
| 9,888,949 B2 | 2/2018 | Johnson et al. |
| 2004/0116930 A1 | 6/2004 | O'Driscoll et al. |
| 2005/0107796 A1 | 5/2005 | Gerlach et al. |
| 2006/0089648 A1 | 4/2006 | Masini |
| 2007/0043367 A1 | 2/2007 | Lawrie |
| 2008/0021475 A1 | 1/2008 | Lawrie |
| 2009/0306724 A1 | 12/2009 | Leither |
| 2010/0198266 A1 * | 8/2010 | Nassab .............. A61B 17/8085 606/280 |
| 2011/0202093 A1 | 8/2011 | Grady, Jr. et al. |
| 2011/0282393 A1 | 11/2011 | Gerlach et al. |
| 2011/0307019 A1 | 12/2011 | Raven, III et al. |
| 2012/0323284 A1 | 12/2012 | Baker et al. |
| 2013/0046347 A1 | 2/2013 | Cheng et al. |
| 2013/0150899 A1 | 6/2013 | Sixto |
| 2014/0214089 A1 | 7/2014 | Glickel |
| 2015/0080970 A1 | 3/2015 | Campbell et al. |
| 2015/0105778 A1 | 4/2015 | Chiu et al. |
| 2015/0142063 A1 | 5/2015 | Austin et al. |
| 2015/0196333 A1 | 7/2015 | Austin et al. |
| 2015/0209091 A1 | 7/2015 | Sixto, Jr. et al. |
| 2015/0223852 A1 | 8/2015 | Lietz et al. |
| 2016/0120581 A1 | 5/2016 | Kay et al. |
| 2016/0128745 A1 | 5/2016 | Sidebotham et al. |
| 2016/0228167 A1 | 8/2016 | Wahl |
| 2016/0249963 A1 | 9/2016 | Guy |
| 2016/0310185 A1 | 10/2016 | Sixto et al. |
| 2016/0367300 A1 | 12/2016 | Caldarella et al. |
| 2017/0065316 A1 | 3/2017 | Castaneda et al. |
| 2017/0095282 A1 | 4/2017 | Ducharme et al. |
| 2017/0189086 A1 * | 7/2017 | Silva .................. A61B 17/8052 |
| 2017/0245904 A1 | 8/2017 | Raven, III et al. |
| 2017/0290670 A1 | 10/2017 | Gorelick |
| 2017/0360453 A1 | 12/2017 | Brailovski et al. |
| 2018/0000528 A1 | 1/2018 | Austin et al. |
| 2018/0036051 A1 | 2/2018 | Ducharme et al. |
| 2018/0049787 A1 | 2/2018 | Davison et al. |
| 2018/0049788 A1 | 2/2018 | Rutledge et al. |
| 2018/0055548 A1 | 3/2018 | Raven, III et al. |

OTHER PUBLICATIONS

Official Communication for EP Patent Application No. 18892351.0 dated Jul. 28, 2021 in 5 pages.

* cited by examiner

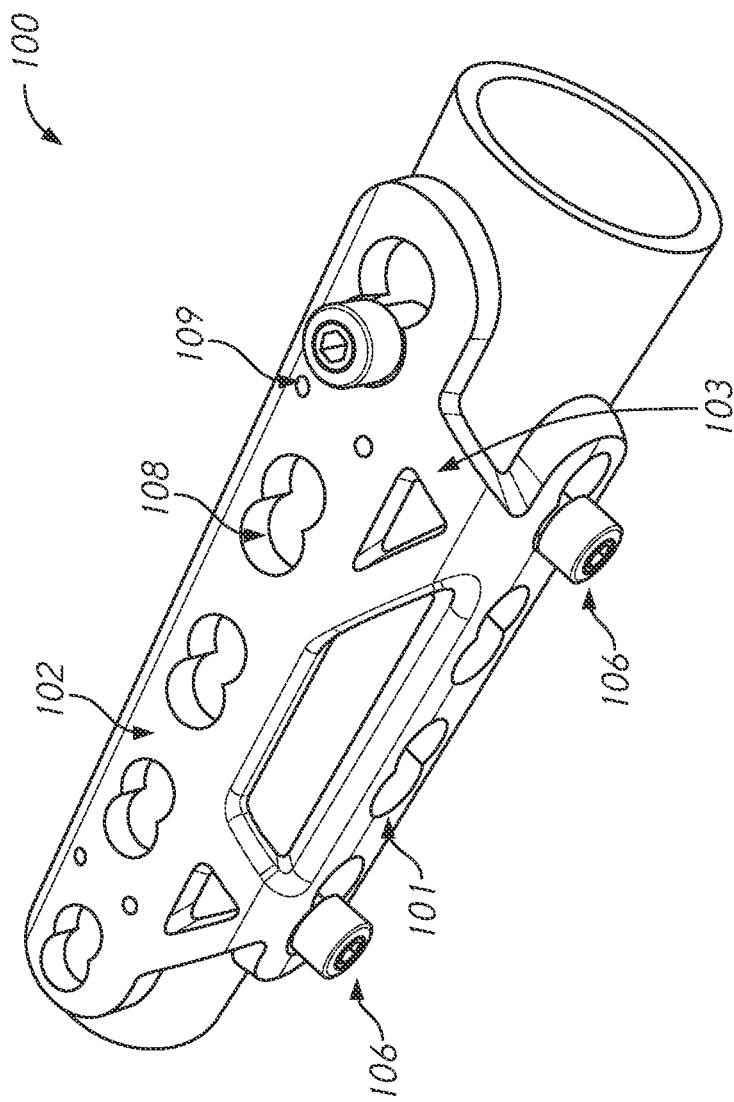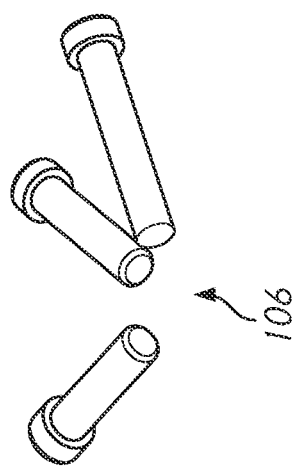
FIG. 3

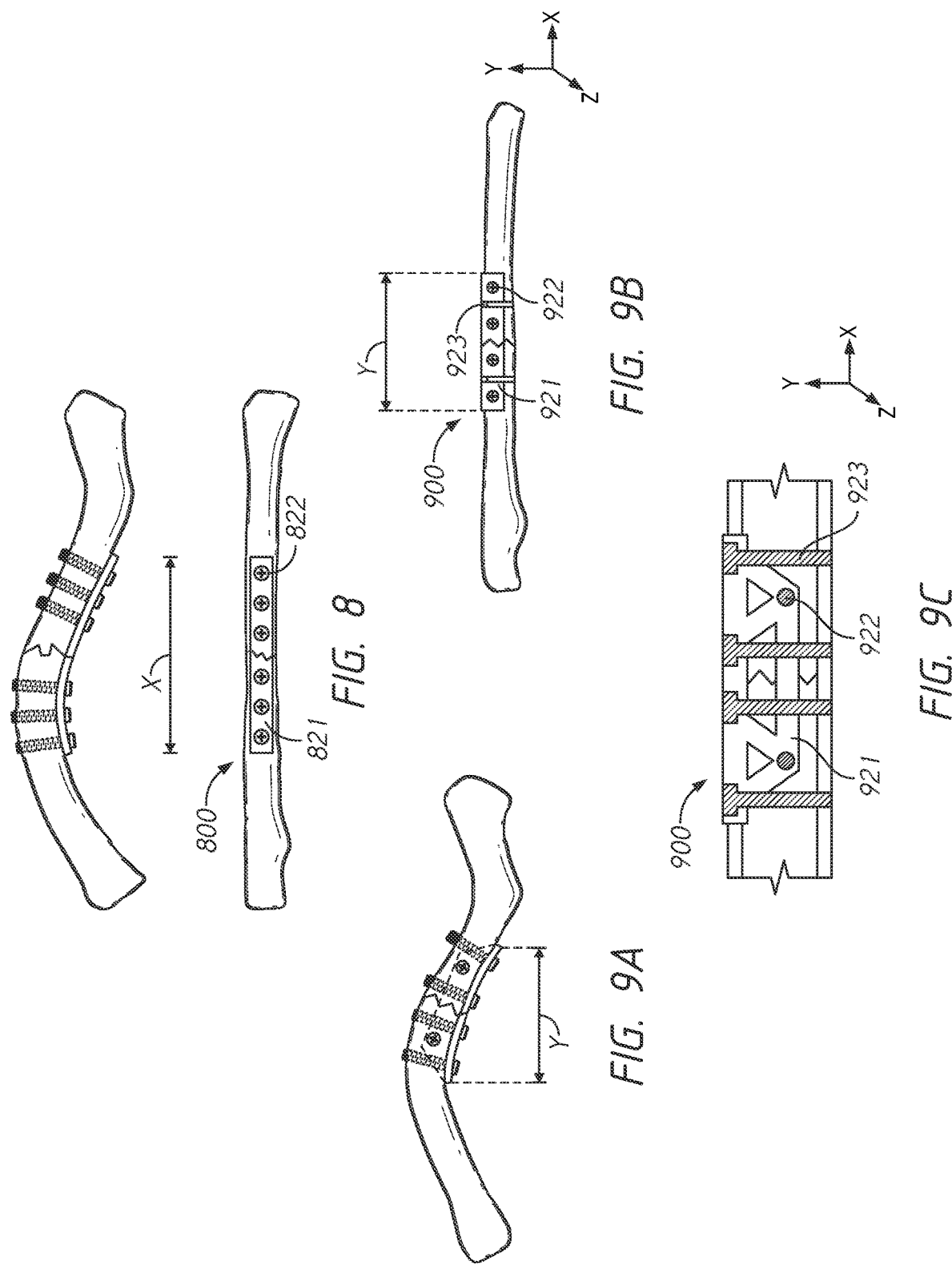

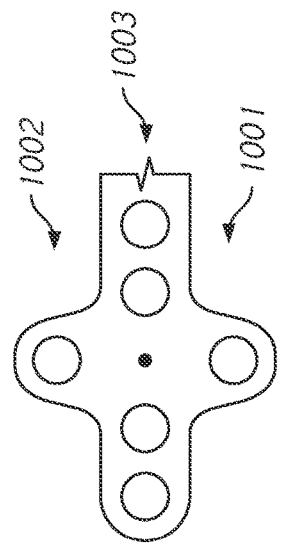
FIG. 10B
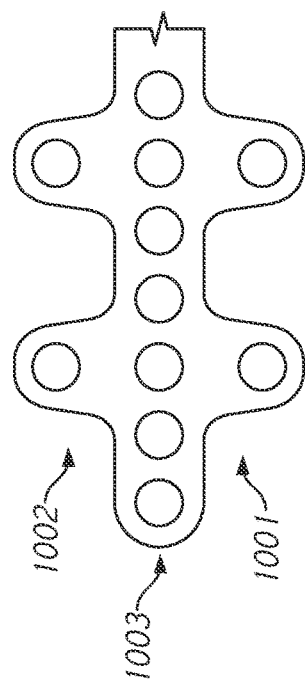
FIG. 10A
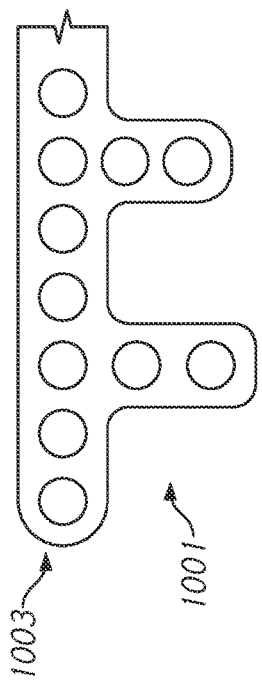
FIG. 10C
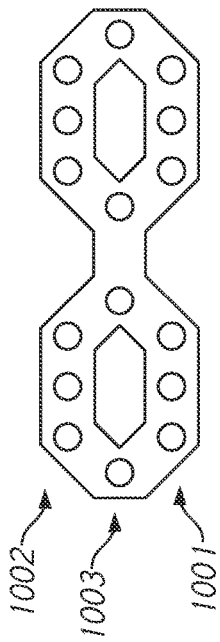
FIG. 10D
FIG. 10E

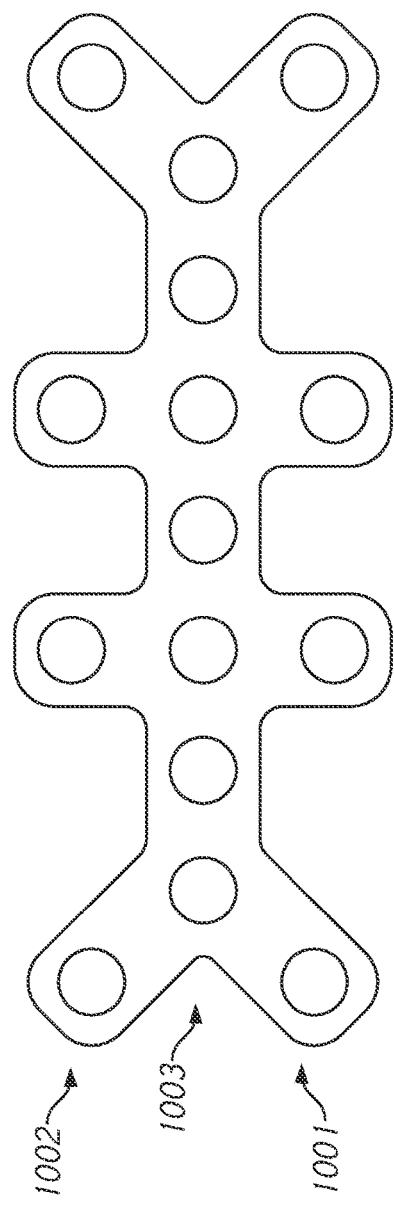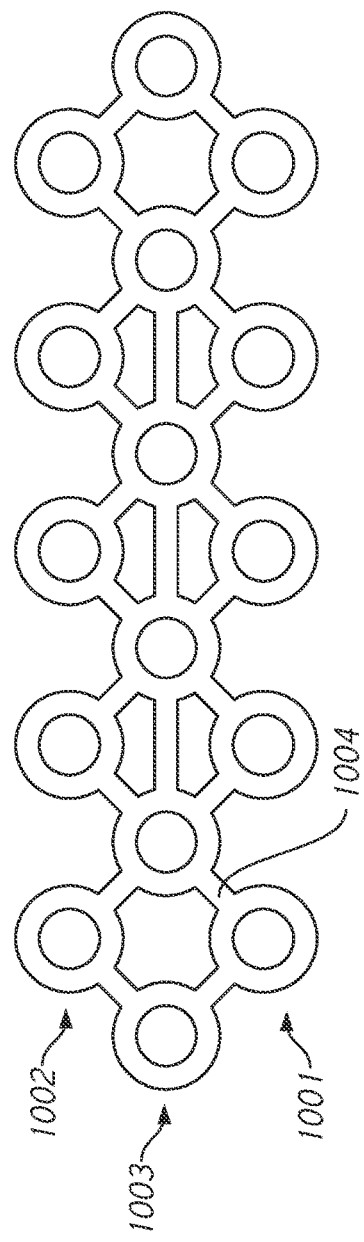
FIG. 10F
FIG. 10G

MULTIPLANAR FIXATION PLATE FOR FRACTURE REPAIR

CROSS-REFERENCE TO RELATED APPLICATIONS

This application claims priority under 35 U.S.C. § 119(e) to U.S. Provisional Application No. 62/655,147, filed Apr. 9, 2018, titled "MULTIPLANAR FIXATION PLATE FOR FRACTURE REPAIR," and U.S. Provisional Application No. 62/608,541, filed on Dec. 20, 2017, titled "MULTIPLANAR FIXATION PLATE FOR FRACTURE REPAIR," which are hereby incorporated by reference herein in their entireties.

BACKGROUND

Field of the Invention

Embodiments described herein relate to innovative surgical devices and methods that can be used to significantly improve clinical outcomes for patients while reducing healing times, reducing costs, and increasing surgical accuracy in bone fracture surgeries. Embodiments of bone surgical devices and methods can be particularly impactful on bone fracture surgeries, including, but not limited to, clavicle fracture surgery.

SUMMARY

According to one embodiment, a clavicle plate fixation system, the system can comprise a plate sized for positioning on a clavicle bone, the plate comprising a first fastening segment, a second fastening segment, and a truss segment, wherein the truss segment connects the first and second fastening segment.

The clavicle plate fixation system of the preceding paragraph or in other embodiments can include one or more of the following features. The first fastening segment can be offset from the second fastening segment at a first angle, wherein the first angle is greater than 60 degrees. The first fastening segment can be orthogonal to the second fastening segment. The first fastening segment and second fastening segment can comprise rounded edges. The truss segment can be curved. The first fastening segment can comprise a first screw hole and the second fastening segment can comprise a second screw hole. The clavicle plate fixation system can further comprise a first screw and a second screw and wherein the first screw is configured to be positioned in the first screw hole and the second screw is configured to be positioned in the second screw hole. The first screw can be configured to be inserted into the bone in a first direction and the second screw can be configured to be inserted into the bone in a second direction and wherein the first direction is offset from the second direction at a second angle, wherein the second angle is greater than 60 degrees. The first screw can be configured to be inserted into the bone in a first direction and the second screw can be configured to be inserted into the bone in a second direction and wherein the first direction is orthogonal to the second direction. The first fastening segment and the second fastening segment can be configured to be bent or curved along a width of the plate to adjust the second angle of the first screw with respect to the second screw. The truss segment can comprise one or more struts connecting the first fastening segment to the second fastening segment. The first fastening segment can have a different shape than the second fastening segment. The first fastening segment can have the same shape as the second fastening segment. The first fastening segment, the second fastening segment, or the truss segment can comprise one or more folds, perforations, gradient curves, indentations, hinge points, or a combination thereof. The first fastening segment, the second fastening segment, or the truss segment can comprise one or more wire or suture holes.

According to another embodiment, a clavicle plate fixation system, the system can comprise a plate sized for positioning on a clavicle bone, the plate comprising a first fastening segment, a second fastening segment, and a central segment, wherein the central segment connects the first and second fastening segment and the first fastening segment and the second fastening segment comprise one or more screw holes, and wherein the first fastening segment is offset from the second fastening segment at a first angle, wherein the first angle is greater than 60 degrees.

The clavicle plate fixation system of the preceding paragraph or in other embodiments can include one or more of the following features. The first fastening segment can be orthogonal to the second fastening segment. The central segment can comprise one or more screw holes. The central segment can comprise one or more cut outs. The central segment can comprise tapered edges. The first or second fastening segment can comprise a tapered distal end. The first fastening segment and second fastening segment can comprise rounded edges. The plate can be curved along a length of the plate. The plate can be curved along a width of the plate. The first fastening segment can comprises a first screw hole and the second fastening segment can comprises a second screw hole. The system can further comprise a first screw and a second screw and wherein the first screw is configured to be positioned in the first screw hole and the second screw is configured to be positioned in the second screw hole. The first screw can be configured to be inserted into the bone in a first direction and the second screw can be configured to be inserted into the bone in a second direction and wherein the first direction is orthogonal to the second direction. The first screw can be configured to be inserted into the bone in a first direction and the second screw can be configured to be inserted into the bone in a second direction and wherein the first direction is offset from the second direction at a second angle, wherein the second angle is greater than 60 degrees. The central segment and the first and second fastening segments can comprise a uniform thickness. The system can further comprise inter-segment connections connecting the fastening segments to the central segments, wherein the inter-segment connections are thinner than the central segment and the first and second fastening segments.

Any of the features, components, or details of any of the arrangements or embodiments disclosed in this application, including without limitation any of the plate fixation system embodiments disclosed below, are interchangeably combinable with any other features, components, or details of any of the arrangements or embodiments disclosed herein to form new arrangements and embodiments.

BRIEF DESCRIPTION OF THE DRAWINGS

Various embodiments of the devices and methods of the present disclosure are described herein with reference to the drawings wherein:

FIG. 3 illustrates a view of an embodiment of the bone fracture system including a bone surgical plate device and surgical screws;

FIG. 8 illustrates a bone with a linear surgical plate system;

FIGS. 9A-9C illustrate embodiments of a bone with a multiplanar surgical plate system with a multiplanar plate and six orthogonal screws;

FIGS. 10A-10G illustrate embodiments of screw hole patterns of a multiplanar surgical plate;

DETAILED DESCRIPTION

Figure 1:
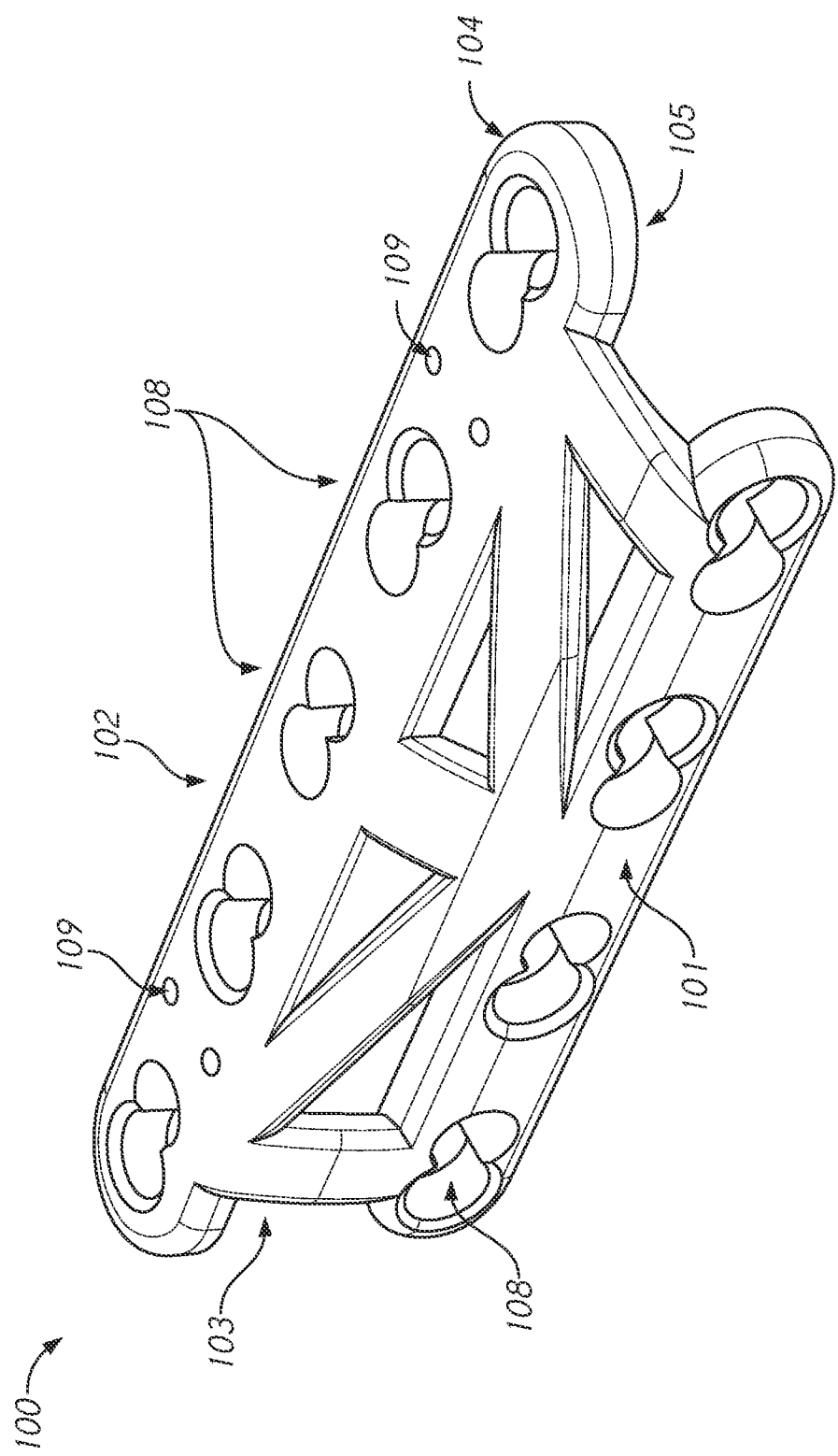
FIG. 1 illustrates an embodiment of a bone fracture system with multiple segments.

Embodiments of the bone surgical plate system can be used for bone fracture surgeries, for example clavicle fracture surgery. The bone surgical plate systems disclosed can be used in whole or in part, with each element or aspect of the system being independently applicable of each other. The system comprises a plate device with specific design features including but not limited to differing designs, geometries, and configurations in the truss segment and the various fastening segments. In some embodiments, the plate device can be made of a material used for surgical implants and surgical plates including, but not limited to, stainless steel and titanium and alloys thereof.

Existing surgical devices for small bone fracture repair can be large, thick, cumbersome, expensive, painful, and short-lasting. Current small bone fracture repair devices on the market can cause irritation and damage to surrounding tissues and nerves. Due to the irritation or damage, these devices have to be removed leading to additional surgeries and excess costs. It can be helpful to use a more stabilizing device that can reduce the tissue and nerve damage, reduce incision size, and minimize the necessity for the device to have to be removed while still maintaining the stabilization and fixation requirements for bone fracture repair, including but not limited to, small bone fracture repair.

For clavicle fracture repair specifically, existing surgical devices are designed to attach to the clavicle in substantially singular regions, such as the anterior, superior, or lateral regions of the clavicle. These existing devices allow for bone screw fixation in a single linear plane or multiple planes that are substantially non-orthogonal and restricted to a single region. For example, even if multiplanar fixation is allowed, screw hole positions in different planes are typically offset by a maximum of 50 degrees (around the circumferences of the bone in the z-axis transverse to the longitudinal axis). Further, existing devices are designed with minimal width (in the z-axis transverse to the longitudinal axis) to keep fixation to a single region of the clavicle. Existing devices, given substantially linear and single region designs, limit the bone screw fixation permutations at a surgeon's disposal.

Embodiments of the bone surgical plate systems are a substantial improvement from existing devices. In some embodiments, a bone surgical plate system can include a bone surgical plate device with multiple segments. The bone surgical plate system can have multiple segments as shown in FIGS. 1 and 2A-2C. As illustrated in these figures, in some embodiments the bone surgical plate device 100 can have at least three distinct areas: the first fastening segment 101; the truss segment 103; and the second fastening segment 102. The distinct segments can have unique geometries that can facilitate insertion, improve rotational control, simplify extraction, create flexible lengths and bend angles, and increase stability of the device. The multiple segment device design, with particular attention to minor design details in each segment, is advantageous for bone surgeries within which the surgeon must operate with a small margin for error around limited space and bone.

The surgical plate system can include multiplanar plates. The multiplanar plates include plates wherein locking screws may enter the bone in more than one plane. The multiplanar plates include plates where locking screws may enter the bone in substantially orthogonal planes (greater than 60 degrees of offset angle from one another). The multiplanar plates include plates where locking screws may simultaneously enter the bone from substantially different regions of the bone (e.g., anterior and superior regions of the clavicle). In some embodiments, the surgical plate system can include pre-curved plates. In some embodiments, the curvature of the pre-curved plates can facilitate multiplanar fixation and/or substantially orthogonal fixation. The surgical plate system can include a central segment (also referred to herein as a truss segment). In some embodiments, the surgical plate system can include a plate with three or more segments. The segments can be centrally connected by the central segment or truss-like segment. Additionally, the surgical plate system can include bendable fastening segments. The bendable fastening segments can include flap-like fastening segments extending from a central segment and the flap-like segments are configured to bend more easily during surgery. The bendable fastening segment can be bent to adjust the angle of the screw entry and/or to fit more snugly along the bone. Given the various design aspects and embodiments, the surgical plate system disclosed herein can allow surgeons to better repair various fracture patterns within a fractured bone (e.g., transverse, butterfly, and comminuted clavicle fractures).

In some embodiments, the surgical plate system can have a pre-curvature along the width of the device.

The bone surgical plate system utilizes the device geometry within different segments within the device that are designed to optimize surgery. In some embodiments, the plate device can include at least the three segments described in embodiments herein. In some embodiments, the device can have one or more truss segments. In some embodiments, the plate device can include a perforation in one or more of the truss segments to aid bending of the device. The plate device can have any number of truss segments and fastening segments that provide for a bent or curved device around the bone to allow for fixation on the bone at more than one angle. The design of the plate device is based on the individual segments as well as how each segment of the device works with respect to one another (and hence, impacts surgery and healing). Described herein is a device with three or more segments, however, the device can be made of any number of segments greater than one. As used herein, the term plate and the term plate device can be used interchangeably to refer to the multi-segment implant.

FIG. 3 illustrates a view of an embodiment of the bone fracture system including a bone surgical plate device 100 and surgical screws 106. The various geometries of the plate device 100, as described further below, are positioned on a small bone, for example the clavicle bone, to prevent rotation and movement within the bone.

The clavicle bones can also have an inner side and an outer side. The outer side of the clavicle refers to the portion of the clavicle directed toward the back or posterior side of the body of the patient. The inner side of the clavicle refers to the portion of the clavicle directed toward the front or anterior side of the body of the patient. The clavicle bone presents a double curvature. The curvature of the clavicle bone can include a convex inner curve in the medial half and a concave inner curve in the lateral half of the clavicle.

As discussed in more detail below, the surgical plate device can have varying geometries that ease insertion while limiting incision size, surgery times, material costs, pain, and the need for implant removal. In some embodiments, the plate device can include flat surfaces. In some embodiments, the plate device can be placed along a bone fracture, to be fastenable to various bone fragments.

As shown in FIGS. 1 and 2A-2C, the plate device can have an outer side 104 and an inner side 105. The outer side of the plate device refers to the side of the plate device directed away from the bone when the device is implanted. The inner side of the plate device refers to the portion of the plate device directed toward the bone when the device is implanted. The outer side 104 and inner side 105 of the device can be flat or curved. The curvature or flat characteristics does not have to be the same between the outer side 104 and the inner side 105. In some embodiments, curvature or flat characteristics of the outer side 104 and the inner side 105 can vary per segment.

FIGS. 2A-2C illustrates various embodiments of the bone fracture system including fastening segments 101, 102 and a truss 103.

FIG. 3 illustrates another embodiment of the bone fracture system including the bone surgical plate device 100 with fastening segments 101, 102 and truss 103 and one or more locking screws 106.

Figure 2:
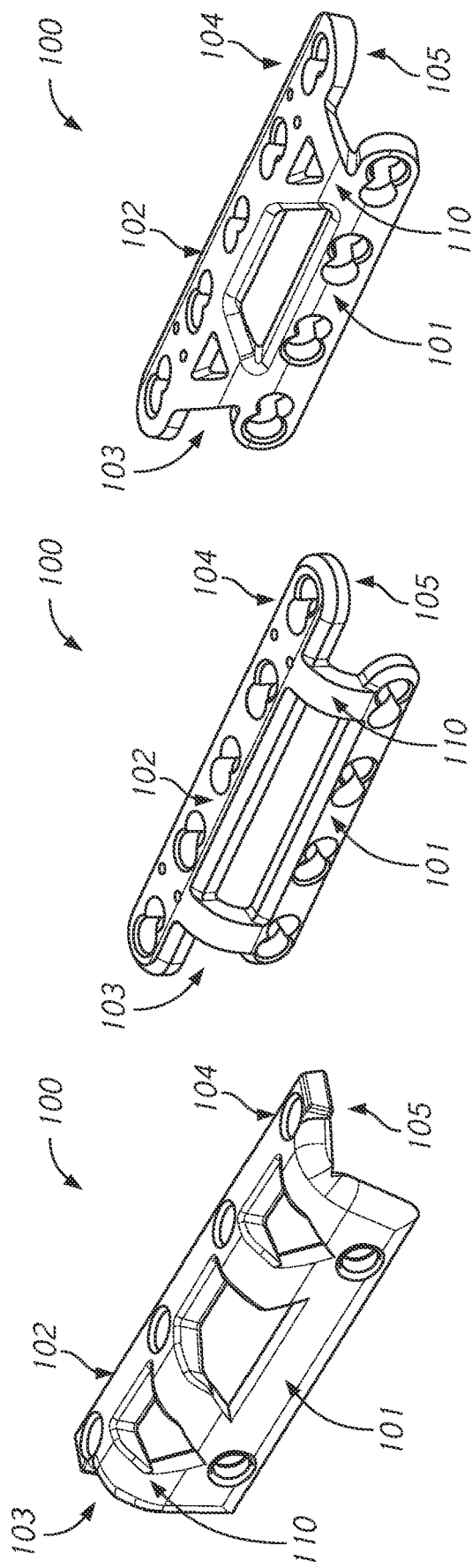
FIGS. 2A-2C illustrate embodiments of a bone fracture system with various geometries.

As shown by FIGS. 1-3, the geometry of the truss can be utilized to ease fastening of the fastening segments to the bone with minimal damage to the surrounding bone, minimal interference with tissue surrounding the bone, and prevent bone fragment movement once fastened.

Figure 4:
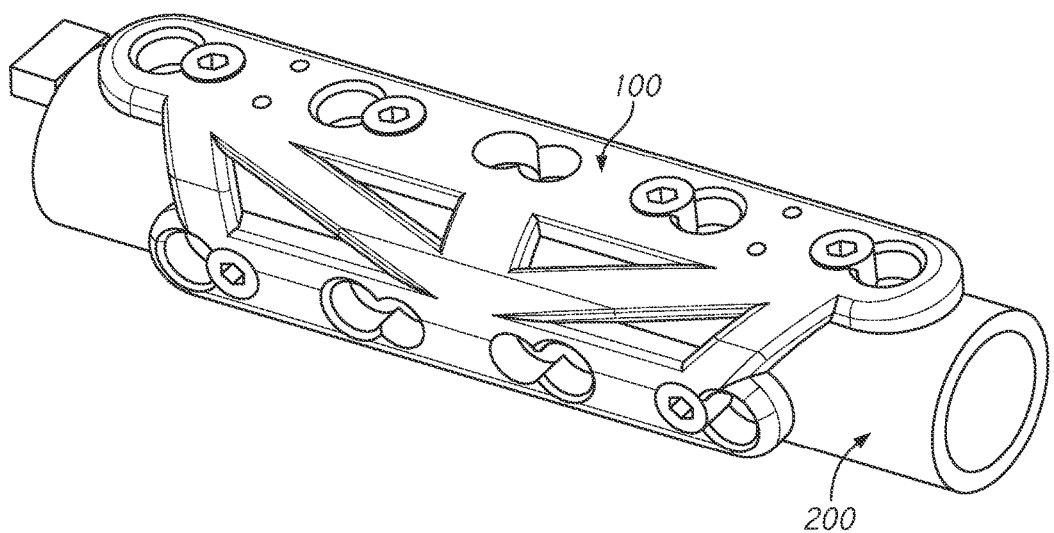
FIG. 4 illustrates an embodiment of a bone fracture system shown on a small bone model.

FIG. 4 illustrates an embodiment of the surgical plate device 100 with the outer/inner sides and medial/lateral ends of the surgical plate device 100 shown on a small bone model 200. As described previously, the plate device 100 can have an inner and outer side that defines the positioning of the plate device 100 on the clavicle bone or other bone. The plate device 100 can have a medial and lateral portion that defines the position along a length of the device that extends from a medial to lateral area of the bone fracture site.

In some embodiments, the bone surgical plate system can have various geometries to accommodate different bone types and sizes. In some embodiments, the fastening segments 101, 102 can have a rounded rectangle shape as shown in at least FIGS. 1 and 2A-2C. In some embodiments, the truss segment 103 can have various shapes and can include one or more struts connecting the first fastening segment 101 to the second fastening segment 102. The various geometries of the multiple segments of the plate device as described herein can include rectangular, rounded rectangular, triangular, S-shaped, scalloped shaped, and/or any other shape utilized for surgical bone plates. In some embodiments, the first fastening segment can have a different shape than the second fastening segment. In some embodiments, the first fastening segment can have a different size than the second fastening segment. In other embodiments, the first fastening segment and the second fastening segment can have the same shape and/or the same size.

In some embodiments, the surgical plate system can be arranged to allow for enhanced engagement with the bone along the length of the plate and to reduce rotational and lateral movement of the bone fracture segments (along with the plate system).

In some embodiments, the truss segment could be comprised of a flat inner and/or outer surface. In some embodiments, the truss segment could be curved.

In some embodiments, at least one fastening segment could be comprised of a flat inner and/or outer surface. In some embodiments, at least one fastening segment could be curved.

In some embodiments, at least one fastening segment and/or truss segment can include one or more folds, perforations, gradient curves, or a combination thereof.

The clavicle bone has a gentle S-shaped curve that varies from person to person. This S-shaped curve can make it challenging to create a device that adapts to the S-shaped curve of the bone and facilitates insertion into the bone.

In some embodiments, the surgical plate device 100 can have a bend that is formed in the plate prior to insertion and/or upon manufacture of the plate device. The pre-bent plate device can adapt to the S-shaped curve and facilitate insertion by adding gentle curvature along a specific axis. The axis can be varied depending on the clavicle bone geometry and whether the plate will be inserted into the left or right clavicle. The pre-bend of the plate device can have a gentle curvature that includes a gentle C-shaped or S-shaped arc to allow for easier passage and control while deploying the plate into the bone. In some embodiments, one or more of the segments of the surgical plate device 100 can be shaped or bent. In some embodiments, all segments in the surgical plate device 100 can be shaped or bent. In some embodiments, a segment of the surgical plate device 100 can have a different geometry or curvature than another segment of the surgical plate device 100. In other embodiments, the curvature or bend in the surgical plate device 100 can be the same through all segments of the device. In some embodiments, the plate device can include one or more perforations in one or more segments of the device to aid bending of the device. The surgical plate device can utilize pre-formed perforations, indentations, hinge points, or any other known technique of pre-bending or bending during a procedure.

The size of the plate can vary depending on the desired results and the surgical procedure and bone fracture being treated as described herein. For example, the human clavicle is highly variable in shape and size and a determination of appropriate implant size can be made.

Fastening Segments:

In some embodiments, the plate device 100 can include a first fastening segment 101 and a second fastening segment 102 with a variety of geometries and screw hole patterns 108.

FIG. 1 illustrates a multiplanar plate with three distinct segments. As shown in FIG. 1, the two fastening segments 101 and 102 (with screw holes 108) are perpendicular to one another. These segments are positioned to allow for orthogonal bi-planar fixation of the bone by a single plate. That 90 degree offset from one another can be adjusted during manufacturing or during surgery to 60 degrees (about 60 degrees), or greater, of offset angle from the most offset fastening segments.

In some embodiments, the first fastening segment 101 and/or a second fastening segment 102 can be similar to surgical plates. In some embodiments, the first fastening segment 101 and/or a second fastening segment 102 can have rounded edges as illustrated in FIG. 1. In some embodiments, the rounded edges can help reduce irritation of the soft tissue or surrounding bone. In some embodiments, the middle of the first fastening segment 101 and/or a second fastening segment 102 can be thicker than the edges as illustrated in FIG. 1.

In some embodiments, the first fastening segment 101, a second fastening segment 102, and/or the truss segment can be a reduced length that is smaller than existing surgical plates which can minimize the incision necessary for the surgery and can also minimize scarring. In some embodiments, the device can be 30 mm to 10 cm (about 30 mm to about 10 cm) for clavicle bone fracture repair. In some embodiments, the incision size for the bone surgical plate system 100 can reduce the incision size by 60% (about 60%) compared to traditional implant devices. In some embodiments, the incision size for the bone surgical plate system 100 can reduce the incision size by approximately 30 to about 60% (about 30 to about 60%) compared to traditional implant devices. An incision size for a traditional implant device can be between 3.5-6 inches. In some embodiments, this can be reduced by anywhere from 20-60% thereby reducing the incision size to a smaller 2-4 inch range.

In some embodiments, the first fastening segment 101 and/or a second fastening segment 102 can have a reduced thickness to decrease the potential for tissue damage and thereby decreasing the necessity for a second surgery.

The multiple fastening segments can allow for the surgical bone plate system to be fastened to a bone or one or more bone fragments through multiple angles and planes. In some embodiments, the first fastening segment 101 and/or a second fastening segment 102 can be personalized or tailored to the patient and/or bone type. The first fastening segment 101 and/or a second fastening segment 102 can be bent with surgical tools and/or during manufacture. As shown in FIGS. 1 and 2A-2C, the first fastening segment 101 and/or a second fastening segment 102 can have one or more screw holes 108. In some embodiments, the screw hole 108 can be a dual hole as illustrated in FIG. 1. The dual hole can allow for the use of a locking screw and/or a compression screw. The one or more holes can allow for options for hole placement to account for different fracture patterns. In some embodiments, the angles of the first and second fastening segments and hole patterns with multiple holes across multiple fastening segments (and planes) can create more permutations of fastening options for the surgeon based on the specific fracture and anatomy being repaired.

In some embodiments, the first fastening segment 101 and/or a second fastening segment 102 can include wire or suture holes 109. The wire or suture holes 109 can be used for guide placement to help secure bone and bone fragments to the device and each other prior to securing the device with the screws. The wire or suture holes 109 can allow for the use of metal wires such as K-Wire and/or sutures. For example, cerclage can be done around bone fragments to hold them together using the wire or suture holes 109.

Truss Segment:

In some embodiments, the surgical plate can have a truss segment that connects multiple fastening segments of the plate. Surgical plates for bone surgery and clavicle fracture surgery can have challenges related to the large implant size, damage to the surrounding tissue or bone, and the short-lasting nature of the device.

The first fastening segment 101 and/or a second fastening segment 102 can be connected with a truss segment 103 as shown in FIG. 1. The centrally located segment in FIG. 1 is a truss segment, designed to connect the two fastening segments with added strength. The truss segment can be thin enough to allow for bending. The truss segment can provide strength and/or stability for the device and the fastening segments. In some embodiments, the first fastening segment 101, a second fastening segment 102, and/or the truss segment 103 can be personalized or tailored to the patient and/or bone type. The truss segment 103 can provide the first fastening segment 101 positioned at an angle offset from the second fastening segment 102. The first fastening segment 101 and/or a second fastening segment 102 can be bent or rotated about a longitudinal axis that passes through the truss segment 103 from the medial to lateral portion the device. The first fastening segment 101 and/or a second fastening segment 102 can be arranged at a specific angle. As used herein, the angle can refer to the angle formed by the planes generally extending through the two fastening segments. In some embodiments, the first fastening segment 101 and/or a second fastening segment 102 can be arranged at an angle where the first and second fastening segments form a 90-degree angle (about 90-degree angle). In some embodiments, the first and second fastening segments can form any angle between a 120-degree angle to a 60-degree angle (about a 120-degree angle to about a 60-degree angle). In some embodiments, the first and second fastening segments can form any angle between a 150-degree angle to a 30-degree angle (about a 150-degree angle to about a 30-degree angle). In some embodiments, the first and second fastening segments can form any angle between a 180-degree angle to a 0-degree angle (about a 180-degree angle to about a 0-degree angle).

In some embodiments, the bent configuration can position the first fastening segment 101 in a different plane than the second fastening segments 102 creating a multiplanar device. For example, in some embodiments, the first fastening segment 101 can be positioned in either an anterior or posterior plane while the second fastening segment 102 is positioned in either an inferior or superior plane. In other embodiments, the second fastening segment 102 can be positioned in either an anterior or posterior plane while the first fastening segment 101 is positioned in either an inferior or superior plane. In some embodiments, the first fastening segment 101 and the second fastening segment 102 can be positioned in different planes at an angle from the anterior, posterior, inferior, or superior planes.

In some embodiments, the truss segment 103 can itself be bendable and/or curved in various planes to fit the bone curvature, for example, the S-shaped curvature of the clavicle bone. In some embodiments, the holes or openings in the truss segment can be used in combination with fixation mechanisms such as screws, wires, and/or sutures to further secure the device.

In some embodiments, the first fastening segment 101, a second fastening segment 102, and/or the truss segment 103 can be bent or manipulated with surgical tools and/or during manufacture. In some embodiments, the ability to bend and adjust the plate in relation to the truss segment can alter the geometry and fastening angles as needed either pre-surgery or mid-surgery. The multiple fastening segments and the truss arrangement of the device can allow for the bone surgical plate system to be fastened to a bone or one or more bone fragments through multiple angles and planes.

In some embodiments, the device 100 can have a 90-90 biplanar fixation for optimal strength. The 90-90 biplanar fixation includes a device where each fastening segment has a flat inner side or flat plane, and those two planes are at a 90-degree angle from each other. The locking screws can then enter the bone via each fastening segment perpendicular to one another—and the inner side of the fastening segments can lay flat against bone in two perpendicular planes to hug the bone securely. The design and angle selected for the multiple fastening segments and the truss segment can balance priorities of plate strength, size, flexibility, fastening segment angles, and/or other characteristics of the system. The bent or angled design can allow for the first fastening segment 101 and a second fastening segment 102 to contact different parts of the bone or different bone fragments. Securing the device to different regions or different bone fragments can improve stability of the device and preventing rotation.

In some embodiments, the device utilizing the truss segment can allow for higher stability while using a shorter length and smaller thickness implant, compared to existing implants. The shorter length and smaller thickness of the device can simplify surgery, decrease incisions, and decrease discomfort/deformation for the patient. In some embodiments, the multiplanar and multi-segment system can cover and contact more surface area of the bone and/or fracture site.

FIGS. 2A-2C illustrate some embodiments for the truss segment. As shown in FIGS. 2A-2C, the truss segments can have different configurations and can interact with the fastening segments in different ways. In some embodiments, two, four, or more struts 110 can be used in the truss segment 103. The struts 110 can be perpendicular to the longitudinal axis of the truss and parallel to each other or at angles to each other. FIGS. 2A and 2C illustrate a truss segment 103 with four struts 110 that connect the first fastening segment 101 to the second fastening segment 102. As shown in FIGS. 2A and 2C, the four struts are arranged at an angle and paired to form V-shapes. As shown in FIGS. 2A and 2C, the struts 110 of the truss can contact the first fastening segment 101 at two locations and contact the second fastening segment 102 at four locations.

FIG. 2B illustrates a truss segment 103 with two struts 110. The two struts are substantially parallel to each other and perpendicular to the longitudinal axis of the truss segment 103. As shown in FIG. 2B, the struts 110 of the truss segment 103 can contact the first fastening segment 101 at two locations and contact the second fastening segment 102 at two locations.

The truss design impacts properties of the overall plate including, but not limited to, strength, stability, and/or bend. In some embodiments, the truss segment can take many other forms that can allow device customization to any type of bone, fracture, and/or anatomy. Any truss design that can achieve and/or alter the plate device properties as described herein can be used in the surgical plate device. In some embodiments, the design elements of one fastening segment and/or truss segment can be mixed and matched with one another. The configuration of the segments is interchangeable to create a broad diversity of available plate designs, with the principles of design described herein to provide the added functionality and control desired to improve clinical outcomes.

Locking Screws:

Plates and screws may back out, migrate, become damaged, or cause discomfort over time, requiring a secondary procedure to remove them. To reduce movement of the plate device, threaded screw holes may be used to allow screws to fasten the plate device to the bone. In some embodiments, non-threaded screw holes may be used. In some embodiments, the offset angle of the first and second segments of the bone surgical plate system can allow for a strategic screw placement that can use smaller screws, thinner screws, and/or less screws to fasten the device. Smaller and less screws can be used due to the increased stability provided by the offset angle configuration of the first and second segments.

All existing, well-known, plate or implant fastening devices and/or techniques may be used to fasten the plate device to the bone.

The bone surgical plate system can be used in various bone procedures. For example, the bone surgical plate system can be used in a clavicle fracture procedure.

Although some details, geometries, and configurations of the device and system are described herein with respect to clavicle fracture surgery, the device can also be used in other types of bone surgeries. For example, the device and systems described herein can be used for ulna surgery.

As described herein, the bone surgical plate system can provide an increased stability which can lessen the need for removal or second surgery. Additionally, the bone surgical plate system described herein can be shorter in length than traditional implants which can allow for a smaller incision and less scaring. Additionally, the bone surgical plate system can cause less patient discomfort and faster/better healing. The bone surgical plate system can be less expensive and can reduce the need for multiple surgeries. In some embodiments, the bone surgical plate system can simplify the surgical procedure reducing the likelihood of mistakes. The bendable feature of the bone surgical plate system can assist the device in adjusting to the anatomy and provide a more tailored and personalized implant device.

Figure 5A:
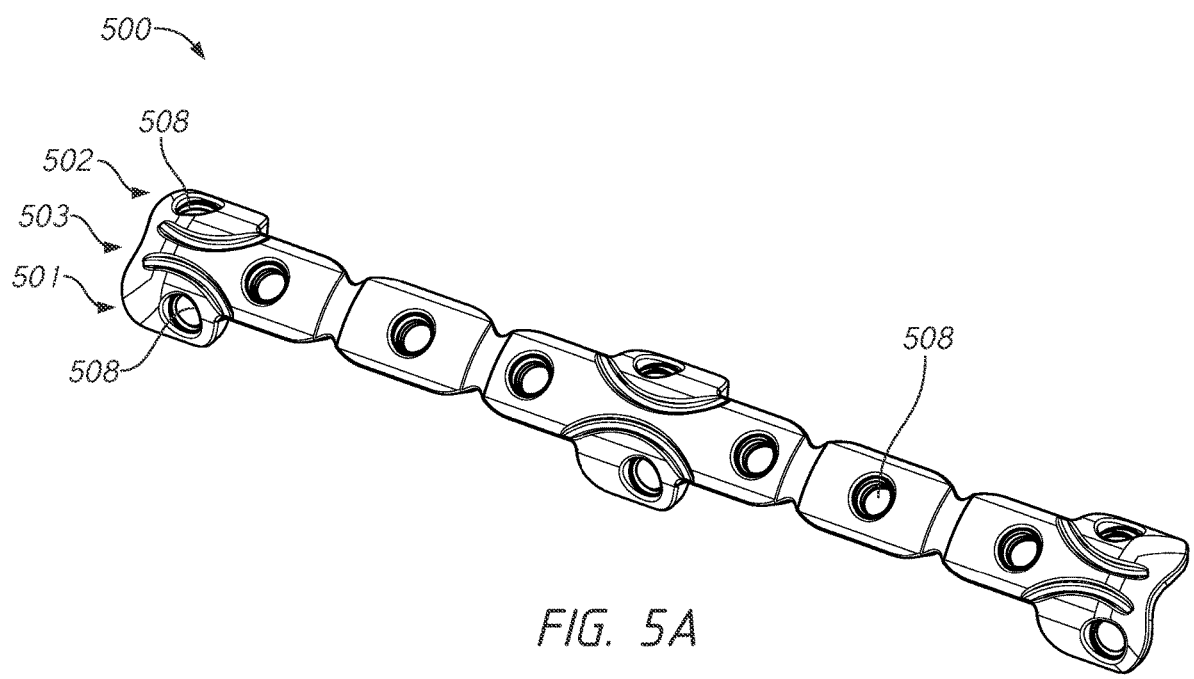
FIGS. 5A-5B illustrate an embodiment of a multiplanar surgical plate system with three distinct planes with screw holes.
Figure 5B:
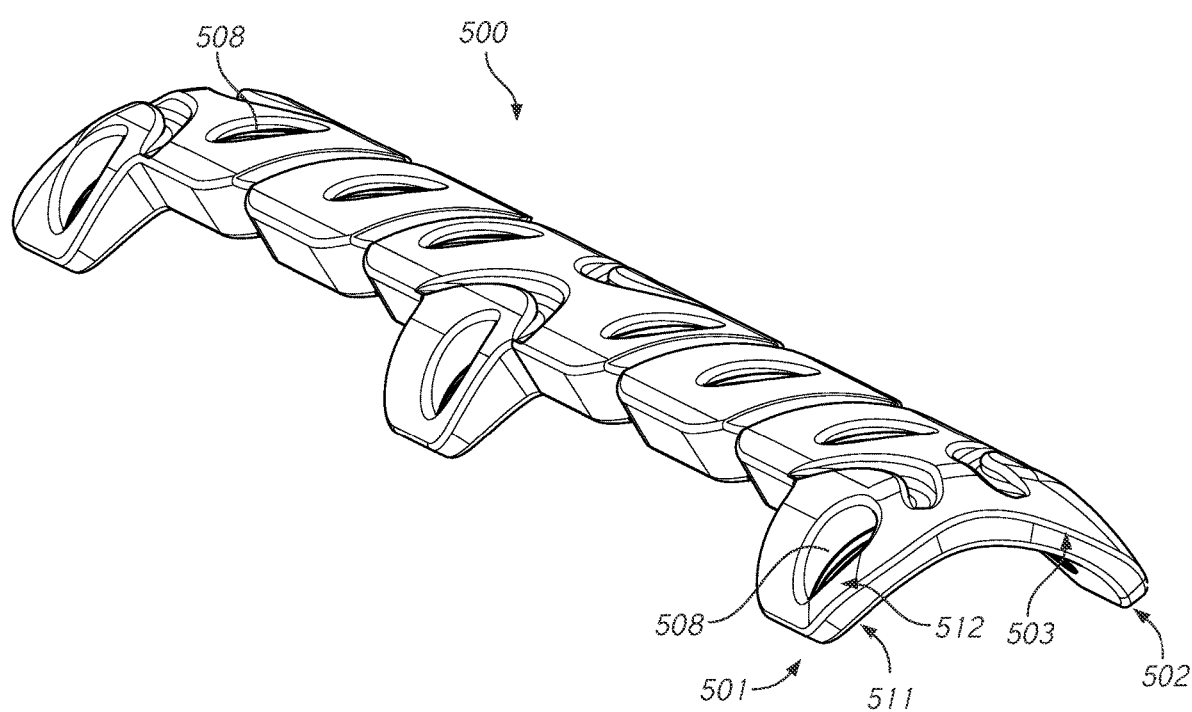

FIGS. 5A-5B illustrate another embodiment of a multiplanar plate. As illustrated in FIGS. 5A-5B, the multiplanar plate 500 can include three distinct planes with screw holes 508 for locking screw fixation. FIG. 5A illustrates a view of multiplanar surgical plate system 500 with a central segment 503 with fastening segments 501 and 502 connected to the central segment 503. The fastening segments 501 and 502 align along two different planes from the central segment. The fastening segments 501 and 502 can align along two different planes from the central segment at greater than 45 degrees (about 45 degrees) offset from one another. The fastening segments 501 and 502 can align along two different planes from the central segment at a greater than 60 degrees (about 60 degrees) of offset angle from one another. As illustrated in FIG. 5A, the central segment 503 as well as the fastening segments 501 and 502 include screw holes 508 for locking screw fixation.

The multiplanar surgical plate includes a thickness defined as the distance from the inner surface 511 to the outer surface 512 of the device as illustrated in FIG. 5B.

The multiplanar surgical plate can have a length that extends from the medial to lateral ends of the device. The length can be parallel to a longitudinal axis of the device that extends through the central segment from the medial to lateral ends of the device.

The multiplanar surgical plate can have a width that is perpendicular to the longitudinal axis of the device and can be measured when the plate is in a linear or non-curved state.

In some embodiments, the fastening segment can have a proximal end at the connection between the fastening segment and the connecting segment and an opposite distal end.

In some embodiments, the multiplanar surgical plate can have a shorter length and bigger width than a traditional surgical plate. In some embodiments, the width of the multiplanar surgical plate can be at least 10 mm wide (at least about 10 mm wide), in the most wide measurement from the distal most end of one fastening segment to the distal most end of an opposing fastening segment. In some embodiments, the multiplanar surgical plate can be greater than 10 mm wide, in the most wide measurement from distal most end of one fastening segment to the distal most end of an opposing fastening segment.

In some embodiments, the length of the multiplanar surgical plate can be 10-40% shorter than the equivalent linear/non-orthogonal device for most surgeries.

In some embodiments, the multiplanar surgical plate can have an average thickness across the device that is less than existing devices. In some embodiments, the desired thickness can be adjusted in any segment or portion of a segment to achieve desired design goals. In some embodiments, the thickness can vary across the multiplanar surgical plate.

It could be expected that the additional width of the device could add to the overall bulkiness of the device leading to a heavier weight, increased difficulty of implant, and more discomfort for a patient. As a result, current "single dimension" clavicle plates can be thin (having a smaller width), thick, and long. Additionally, current clavicle plates may only attach in the anterior, superior, or lateral aspect of the clavicle. Current clavicle plates are substantially linear, connecting to the bone in a single dimension or two planes that are close to one another (close in distance and offset angle, functionally similar to purely linear plates). The multiplanar surgical plate system described herein is used to fix at least two dimensions (for example, anterior and superior parts) of the bone at the same time. The multiplanar surgical plate system described herein can provide a reduction in length and thickness of device compared to existing devices. For example, a common traditional clavicle fixation plate for a large adult clavicle measures 120 mm long, 8 mm wide, and 3.5 mm thick. In some embodiments, of the multiplanar plate system described herein, for an equivalently sized patient, can measure 85 mm long, 13 mm wide, and 2.5 mm thick. Clavicle plating systems come in many sizes to accommodate different sized patients. Similar relative differences in dimensions exist between traditional clavicle plates and the multiplanar plates disclosed herein, regardless of the size of the patient. Additionally, the multiplanar surgical plate system described herein can be used for lateral clavicle fractures as well as diaphyseal fractures. The improved fixation can be accomplished at least by allowing an orthogonal fixation (in the range of 90 degrees fixation) of the bone.

The multiplanar surgical plate system can provide various advantages during and/or after the surgical procedure as well as provide advantages to the patient for healing and recovery. The multiplanar surgical plate system described herein can provide a shorter implant length which can minimize scar sizes and reduce pain. Faster and easier surgeries for both patient and surgeon can be performed utilizing the multiplanar surgical plate system described herein. The improved fixation can be due to the reduction in micromotion of fragments which will reduce scarring and provide a faster bone healing. Shorter healing times can provide a patient with less recovery post-surgery and faster return to everyday functions. Additionally, the lower profile and reduction in irritation can reduce the likelihood that the device will need to be removed, reduce pain, eliminate the possible exposure to a second surgery and second round of anesthesia, and/or reduce the time of non-use of the injured site.

FIG. 5B illustrates a side perspective view of the multiplanar surgical plate system 500 illustrated in FIG. 5A. The multiplanar surgical plate system 500 of FIGS. 5A-5B is similar to the surgical plate system described with reference to FIGS. 1-4. The multiplanar surgical plate systems 500 of FIGS. 5A-5B utilize a central segment 503. The fastening segments 501 and 502 can connect to the central segment 503. Various connections designs can be utilized to connect the central segment to the fastening segment. The particular central segment and fastening segment connection design can depend on the amount of curvature desired for the device and the desired contact or interaction of the device to the bone. The central segment 503 can have various shapes and patterns. The length, width, and thickness of the central segment can be adjusted to minimize bulk and circumferential pressure on the bone to maximize nutritional supply to the bone. In some embodiments, the central segment can be made wider to assist with reduction and alignment for very unstable or segmental fractures. In some embodiments, the central segment can be tapered along the length of the plate to place the thickest portion of the central segment over the fracture site. The tapered outer edges can minimize soft tissue irritation. In some embodiments, the central segment can have cutouts and/or perforations and screw holes 508. The screw holes of the central segment can be optional.

FIG. 5B shows the three planes of the multiplanar plate and the offset angle of the two fastening segment planes (for example, 45 degrees of offset). FIG. 5B illustrates the pre-curvature design of the plate which creates at least three distinct planes for bone screw fixation. In some embodiments, the device can include a pre-curvature or be curved or bent during implantation along the length of the device. In such embodiments, the length of the device can be curved to match the curvature of the bone (for example, the clavicle). In some embodiments, in the transverse axis (transverse to the longitudinal axis) the curvature does not have to be uniform. In some embodiments, multiplanar plate can be precurved to act as a better "frame" or "guide" to align fracture bone segments.

FIG. 5B illustrates the central segment 503 and the fastening segments 501 and 502 forming the three planes. The offset angle of the two fastening segment planes from the central segment can be greater than 60 degrees (about 60 degrees) of offset. The offset angle of the two fastening segment planes from the central segment can be 60 degrees (about 60 degrees), 65 degrees (about 65 degrees), 70 degrees (about 70 degrees), 75 degrees (about 75 degrees), 80 degrees (about 80 degrees), 85 degrees (about 85 degrees), 90 degrees (about 90 degrees), 95 degrees (about 95 degrees), 100 degrees (about 100 degrees), 105 degrees (about 105 degrees), 110 degrees (about 110 degrees), 115 degrees (about 115 degrees), 120 degrees (about 120 degrees), 125 degrees (about 125 degrees), 130 degrees (about 130 degrees), 135 degrees (about135 degrees), 140 degrees (about 140 degrees), 145 degrees (about 145 degrees), 150 degrees (about 150 degrees), 155 degrees (about 155 degrees), 160 degrees (about 160 degrees), 165 degrees (about 165 degrees), 170 degrees (about 170 degrees), 175 degrees (about 175 degrees), 180 degrees (about 180 degrees), or greater than 180 degrees of offset.

In some embodiments, the first fastening segment and/or a second fastening segment can be arranged at an angle where the first and second fastening segments are offset at a 90-degree angle (about 90-degree angle). In some embodiments, the first and second fastening segments can be offset from each other at any angle greater than 60 degrees (about 60 degrees). In some embodiments, the first and second fastening segments can be offset from each other at any angle between a 150-degree angle to a 60-degree angle (about a 150-degree angle to about a 60-degree angle). In some embodiments, the first and second fastening segments can be offset from each other at any angle between a 180-degree angle to a 60-degree angle (about a 180-degree angle to about a 60-degree angle). In some embodiments, the first and second fastening segments can be offset from each other at any angle greater than 180 degrees (about 180 degrees).

In some embodiments, the fastening segment can have a proximal end at the connection between the fastening segment and the connecting segment and an opposite distal end. In some embodiments, the fastening segments 501 and 502 can have a thickness that is thinner toward the distal most edges of the fastening segments to decrease size and increase bendability. FIG. 5B illustrates the tapered or thinner distal most edges of the fastening segments. In other embodiments, the fastening segments 501 and 502 can be a uniform thickness throughout the segment. In some embodiments, the multiplanar plate can have a smaller thickness in one or more segments of the plate. In some embodiments, the inter-segment connections (i.e. connections between the fastening segments and central segment) can have a smaller thickness.

The embodiments described herein illustrate various fastening segments and central segments designs and screw hole patterns. However, any combination of fastening segment and central segment design and screw hole pattern can be used to provide the multiplanar orthogonal (substantially orthogonal) or greater than 60 degree offset angle fixation, described herein.

The multiplanar plate system as illustrated in FIG. 5A-5B can include the central segment 503 with screw holes 508 for direct bone fixation through the central segment 503. In some embodiments, the central segment 503 can include six screw holes or fastening segments 508 as illustrated in FIGS. 5A-5B. In some embodiments, the screw holes 508 can be evenly distributed from the medial side to lateral side of the device. As illustrated in FIG. 5A, the six screw holes 508 within the central segment can have three screw holes 508 on the medial end and three screw holes on the lateral end of the central segment. In other embodiments, screw holes 508 can be distributed in any pattern or spacing.

In some embodiments, the multiplanar plate system can contain three segments that each contain six or more screw holes for bone fixation. In some embodiments, two or more fastening segments contain six or more screw holes in substantially orthogonal positions from one another. In some embodiments, the two or more fastening segments contain screw holes that are positioned in alternating pattern from one another to prevent bone screw interference and offer the surgeon optimal orthogonal bone screw position options. There are no limits to the number of screw holes, planes, or fastening segments. In the above example with three segments, in three separate planes, each containing six screw holes, there are an exponentially large number of bone screw permutations for the surgeon to choose from. For example, assuming the surgery required one bone screw placed in each of the three segments, the surgeon would have 216 (6^3) different 3-bone screw configurations to choose from. In some embodiments, the fastening segments or the central segment can be tapered along the length of the segment to place the thickest portion of the central segment over the fracture site. In some embodiments, the fastening segments or central segments can be tapered along the width of the segment. In some embodiments, the fastening segments and central segments can have various thicknesses throughout the device. The various thickness and tapered outer edges can minimize soft tissue irritation and/or assist or hinder bendability of the segment.

Having so many options for a surgeon, specifically from substantially orthogonal planes and multiple regions of a bone, leads to improved results and patient outcomes, faster, quicker, more effective surgery, faster healing times, and lower removal rates for patients. In some instances, using a single device also prevents surgeons from using multiple implants to try to accomplish some of the benefits achieved by a single multiplanar plate disclosed herein. One example is adapting a multiplanar plate system to common fracture patterns for a given bone fracture. As an example, some common clavicle fractures are transverse, butterfly, and comminuted fractures.

Figure 5C:
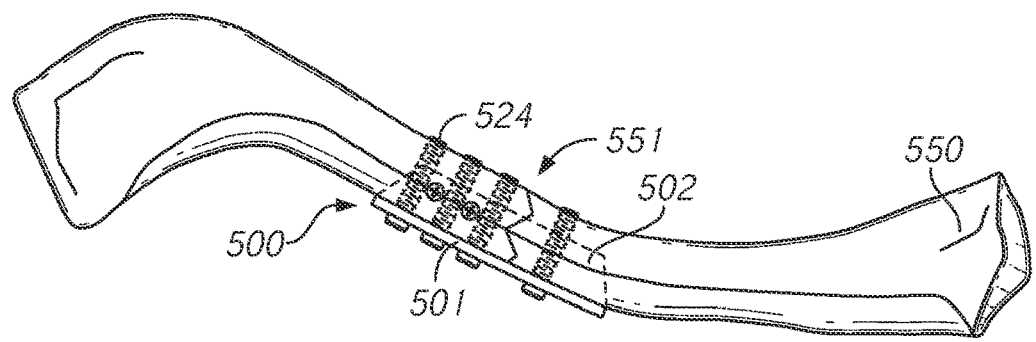
FIGS. 5C-5H illustrate embodiments of a multiplanar surgical plate system.
Figure 5D:
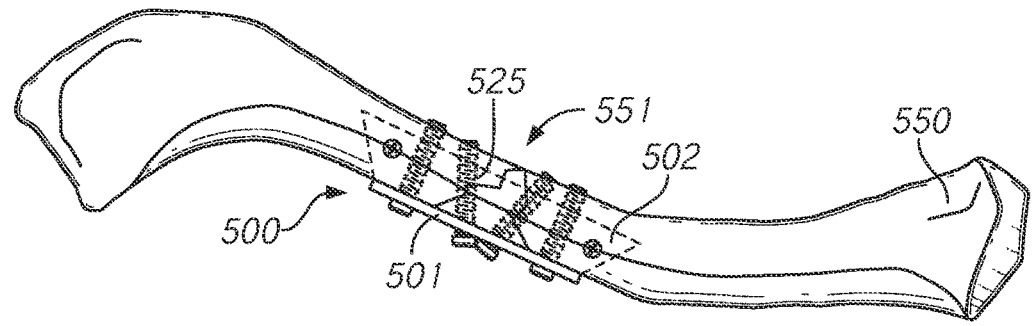
Figure 5E:
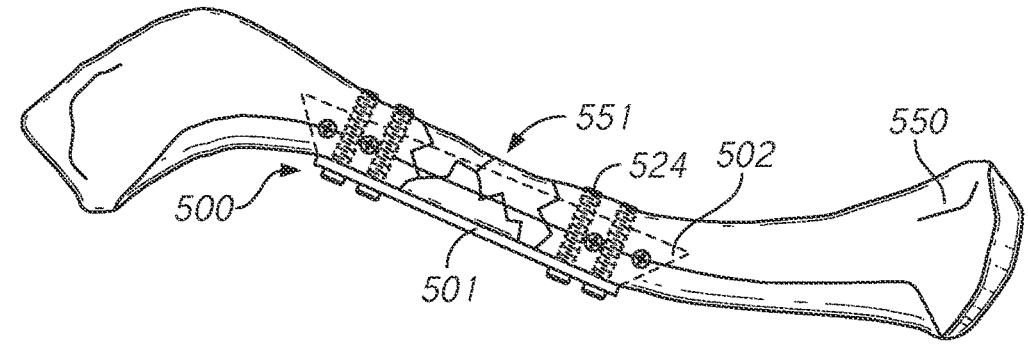

FIGS. 5C-5E illustrate embodiments of the multiplanar surgical plate 500 positioned on a bone 550 over a fracture site 551. The multiplanar surgical plate 500 can utilize the fastening segments 501 and 502 (shown behind the bone), connecting segment (not shown), and screws 524. As illustrated in FIGS. 5C-5E, multiplanar surgical plate 500 can be positioned on both the medial and lateral sides of the fracture site 551. Additionally, the multiplanar surgical plate 500 can provide the fastening segments or central segment on a least two different surfaces. The multiplanar surgical plate system described herein can be used to fix the bone in at least two dimensions (for example, posterior and inferior surfaces as illustrated in FIGS. 5C-5E) of the bone at the same time.

For transverse fracture patterns illustrated in FIG. 5C, the multiplanar surgical plate 500 can allow for short segment multiplanar fixation followed by compression via eccentric screw placement on the other side of the fracture. For example, FIG. 5C illustrates an embodiment of the multiplanar surgical plate 500 positioned on a bone 550 over a transverse fracture site 551. The multiplanar surgical plate 500 can have a multiplanar locking construct and can compress the fracture through the plate. The multiplanar surgical plate 500 can have screws on both sides of the fracture site through fastening segment 501 and can have only screws on one side of the fracture site on the fastening segment 502 as illustrated in FIG. 5C. The multiplanar surgical plate can allow for positioning of screws on one or both sides of the fracture and on one or more surfaces of the bone in contact with the plate.

In the case of short oblique or "butterfly" fractures illustrated in FIG. 5D, the multiple off-angle options of this multiplanar surgical plate 500 can allow for lag screws 525 (interfragmentary compression) through the plate 500 for a more ideal mechanical construct. The multiplanar surgical plate system can provide the ability to lag fragments through the plate. The multiplanar surgical plate system can provide many options for neutralization through short segments. In some embodiments, the multiplanar surgical plate system can include screws that extend across the fracture site. For example, as illustrated in FIG. 5D, the first fastening segment 501 can include two screws that extend across the fracture site as well as two screws on each fastening segment 501 and 502 that are orthogonal to each other.

As illustrated in FIG. 5E, for long segment comminuted fractures, the multiplanar surgical plate 500 can allow for bridging and fixed angle constructs. The multiplanar surgical plate 500 can provide a bridge over the fracture site 551 with fixed-angle screws but no compression. In some embodiments, as illustrated in FIG. 5E, the multiplanar surgical plate 500 can have two pairs of orthogonal screws on each side of the fracture site 551 but no screws going through the fracture.

Figure 5F:
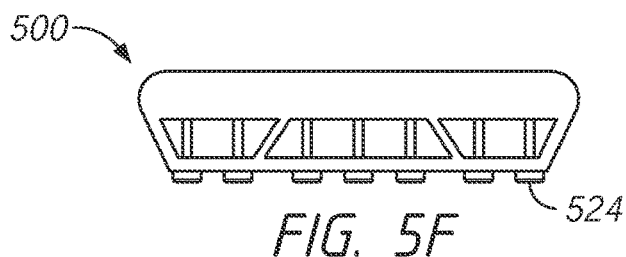
Figure 5G:
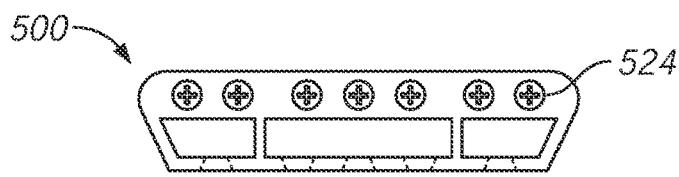

FIGS. 5F-5G illustrate multiple views of embodiments of the multiplanar surgical plate 500 that can provide the biplanar fixation described herein. The plate 500 is shown with seven parallel screws 524 extending across and behind the device in FIG. 5F. FIG. 5G illustrates another view of the multiplanar surgical plate 500 shown with seven parallel screws 524 extending into the page. The screws 524 can be arranged in any number and any pattern. For example, the screws 524 and corresponding screw holes can be evenly distributed throughout the segment of the multiplanar surgical plate 500 as illustrated in FIG. 5F. In other embodiments, the screws 524 and corresponding screw holes can be grouped together in portion of the segment of the multiplanar surgical plate 500 as illustrated in FIG. 5G.

Figure 5H:
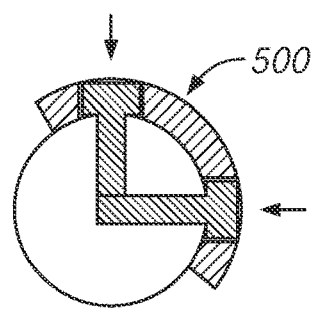

FIG. 5H illustrates a cross-sectional view of the multiplanar surgical plate 500 with an orthogonal or substantially orthogonal offset of fastening segments and/or screws. FIG. 5H illustrates a 90 degree offset screw configuration.

In some embodiments, the multiplanar plate system may act as a guide/brace or "bone fragment positioner" for the surgeon during surgery. In some embodiments, said brace effect can also help patient healing and reduce implant removal rates. Given the expanded width of the multiplanar plate system (into multiple bone regions), compared to existing devices, multiple segments may be designed to place fractured bone fragments in more optimal positions for healing. For example, a truss (or central) segment adapted to contact the fracture site in combination with fastening segments adapted to contour a significant portion of the bone (more than 60 degrees around the circumference of the bone) can create the brace effect. In some embodiments, pre-curving the plate to match the shape of the clavicle can help create the brace effect. In some embodiments, pre-curving the fastening segments in the z-axis (transverse to the longitudinal axis) to be slightly less curved than the underlying bone can allow the bracing effect to be used more practically by the surgeon, because the additional space may allow bone fragments to be aligned more easily (prior to bending the fastening segments down against the bone).

In some embodiments, the design elements related to the brace effect can be balanced with the need to reduce device bulk and reduce device contact with the bone. Reduction of device bulk helps keep the device pliable and easy to enter a smaller incision site. It can also help with patient comfort. Minimizing plate contact with the bone can help maintain circulation within the bone post surgery, which promotes healing of the fracture site. In some embodiments, using cutouts within some or all segments can help reduce bulk and contact with the bone. In some embodiments, using truss-style designs or web-styles designs can help reduce bulk and bone contact. In some embodiments, maximizing the number of screw holes within the given space can achieve these goals while also maximizing screw fixation options.

As described with reference to FIGS. 1-4 previously, the multiplanar surgical plate system of FIGS. 5A-5B can provide a shorter length and/or width of the device leading to decreased incision size. The multiplanar surgical plate system of FIGS. 5A-5B can also include a stronger fixation with multiple planes of direct bone fixation by providing three or more planes for fixation. The multiple fastening segments with the unique design can allow a surgeon or user the flexibility to bend segments to match various fracture types and/or to fit snugly against the bone. The flexibility and ability to fit the multiplanar surgical plate system to the bone can reduce pain and deformation of the device and reduce the need for removal of the device.

Figure 6A:
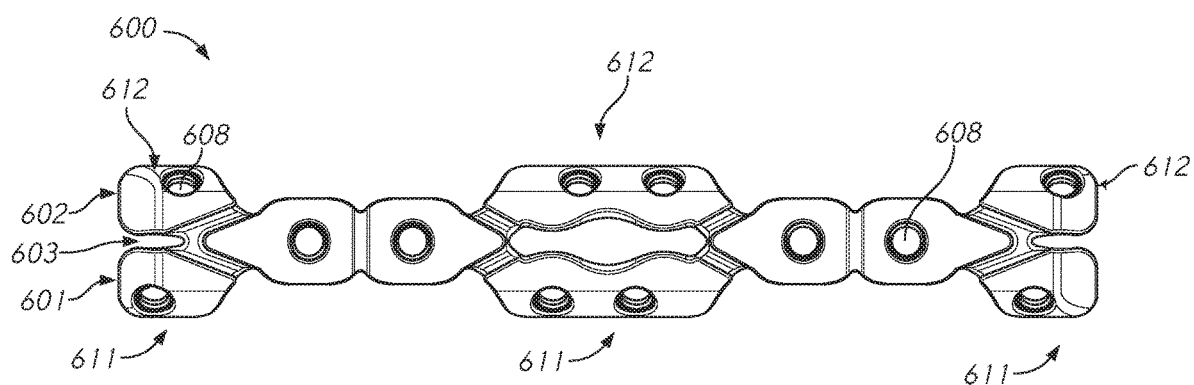
FIGS. 6A-6B and 7 illustrate an embodiment of a multiplanar surgical plate system with three distinct planes with screw holes.
Figure 6B:
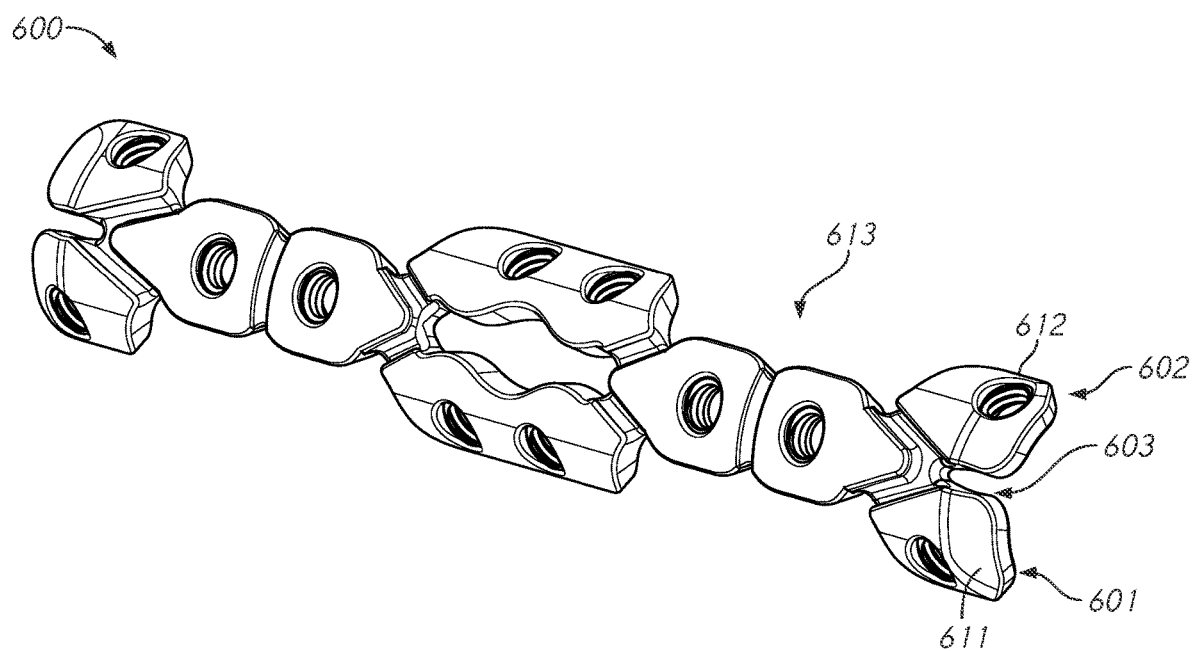

FIGS. 6A-6B illustrate another embodiment of the multiplanar surgical plate system 600 with at least three distinct planes with screw holes 608 for locking screw fixation. FIG. 6A shows the central segment 603 with various fastening segments 601 and 602 connected to the central segment 603. The fastening segments 601 and 602 align along two different planes from the central segment 603. Similar to embodiments described herein, the fastening segments 601 and 602 can align along at least two different planes from the central segment 603 at between a 45 degree to 135 degree (about 45 degree to about 135 degree) offset from one another.

FIG. 6B illustrates a perspective view of the multiplanar surgical plate system in FIG. 6A. FIG. 6B illustrates the central segment 603 and the fastening segments 601 and 602 forming the three planes. The offset angle of the two fastening segment planes (about 45 degrees of offset) is shown in FIG. 6B. As illustrated in FIG. 6B the multiplanar surgical plate system can include a pre-curvature design of the plate that is curved prior to surgical use. In other embodiments, the multiplanar surgical plate system can be bent or curved by the clinician or surgeon prior to implantation or during implantation of the device. Additionally, the fastening segments 601 and 602 can be bendable flap-like segments configured to bend during surgery. The fastening segments 601 and 602 can be bent or curved to adjust the angle of screw entry and/or fit more snugly along the bone. Cutouts within any segment, such as the space between arms 611 and 612, can be strategically placed to maximize bendability while simultaneously decreasing bulkiness and bone contact surface area of the plate. For example, as depicted in FIG. 6A, a cutout can be placed right in the center of the central segment 603 to allow for greater bendability of the middle arms 611 and 612. For certain fracture types, the middle portion of the plate will be placed onto the fracture site, thus decreasing the functionality of plate material (and screw hole option) in the middle of the device. Similarly, other portions of the central segments or fastening segments may be strategically cutout. Due to the multiplanar design of the device, the plate systems herein can maintain strength and durability, improve rotational stability of the fractured bone, increase surgeon placement and fastening options, increase malleability to the bone shape—and simultaneously limit the bulkiness of the plate system in critical dimensions such as thickness and length.

The multiplanar surgical plate system of FIGS. 6A-6B is similar to the system described with reference to FIGS. 5A-5B but the fastening segments connect to the central segment in a different formation. The fastening segment 601 has arms 611 and fastening segment 602 has arms 612. The arms 611 and 612 have a proximal end that is connected to the central segment 603 and a distal end that contains a screw hole 608. The arms 611 and 612 connect to the central segment at an angle. For example, an axis extending from the proximal end to the distal end of the arm can pass through the longitudinal axis of the central segment at a connecting angle between 20 degrees to 160 degrees (about 20 degrees to about 160 degrees). In the configuration shown in FIGS. 6A-6B, the arms 611 and 612 of the fastening segments 601 and 602 are attached to the central segment 603 forming an "X" shape at the edges of the device.

However, the fastening segments can be attached in any formation or along any part of the central segment.

The central segment 603 has a length from medial to lateral ends of the segment. The fastening segments 601 and 602 have a length that is measured from the distal most end of the medial most arm to the distal most end of the lateral most arm. As illustrated in FIGS. 6A-6B, the fastening segments 601 and 602 can have a greater length than the central segment 603. In other embodiments, the fastening segments 601 and 602 and the central segment 603 can be the same length.

The central segment 603 can have fewer screw holes 608 than the fastening segments 601 and 602 as shown in FIG. 6A. The central segment can have cutouts to impact bendability of the device. In some embodiments, as shown in FIGS. 5A-5B and 6A-6B, the multiplanar surgical plate device can include flap-like arms 613 extending from the central segment 603. The flap-like arms 613 can be similar to the arms 611 and 612 without bone screws. The flap-like arms 613 can be contoured to the bone and assist in securing the device to the bone and preventing movement of the device after implantation. In some embodiments, the screw holes 608 can be of smaller diameter (e.g., 2.7 mm) in more regions of the plate compared to existing plate systems. Using smaller screws, while maintaining bone stability and plate system strength, can result in faster healing and increased patient comfort.

Figure 7:
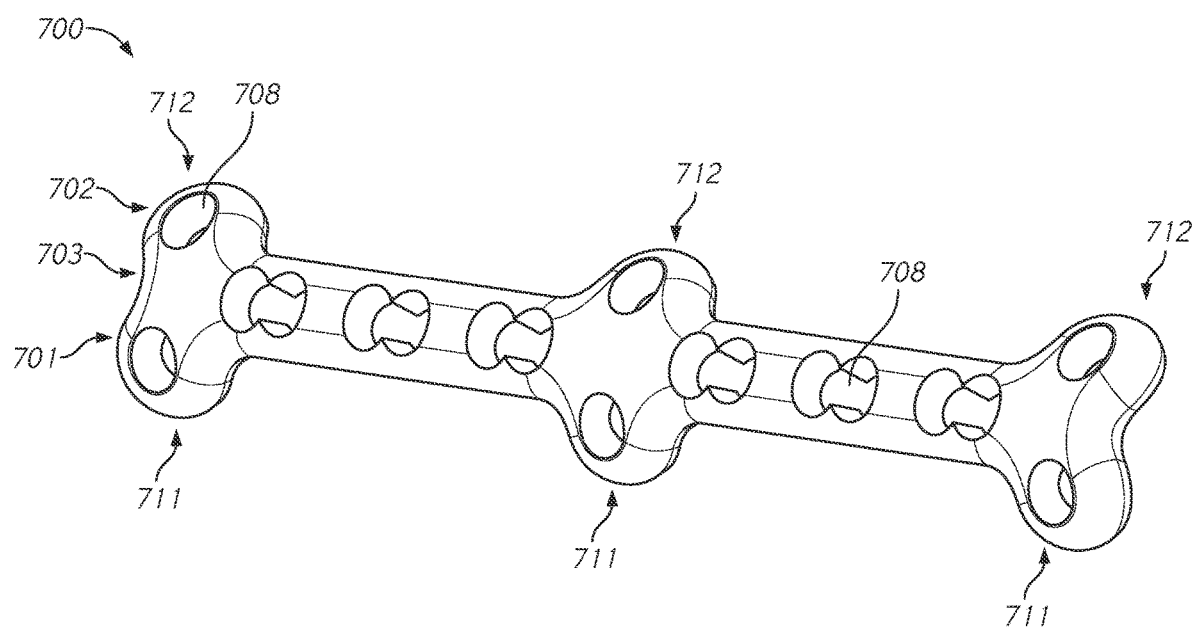

FIG. 7 illustrates an embodiment of a bone fixation device. The device is similar to the device described with reference to FIGS. 5A-5B and 6A-6B but with a different central and fastening segment design. The multiplanar surgical plate system 700 as illustrated in FIG. 7 includes fastening segments 701 and 702 and a central segment 703. The fastening segments 701 and 702 have arms 711 and 712 with screw holes 708. The central segment 703 can have screw holes 708 that are offset from the arms 711 and 712 of the fastening segments as shown in FIG. 7.

As illustrated and described in the embodiments herein, the first fastening segment can be offset from the second fastening segment at an angle as described herein. The first fastening segments and the second fastening segments are illustrated in FIGS. 5A-5B, 6A-6B, and 7 as offset from each other, however, the angle of offset illustrated in these figures should not be limiting and represent only an illustration of the curvature and offset of the device.

FIG. 8 illustrates a small bone (for example, a clavicle bone) with a linear surgical plate system 800 that utilizes a linear surgical plate 821 and six substantially parallel screws 822. The linear surgical plate 821 can have a length X as illustrated in FIG. 8.

FIGS. 9A-9C illustrate embodiments of the multiplanar surgical plate system 900 with a multiplanar plate 921 and six orthogonal screws. The multiplanar plate 921 can have a length Y as illustrated in FIG. 9A. The length X of the linear plate 821 is greater than the length Y of the multiplanar plate 921, however, the multiplanar surgical plate system can provide equivalent or substantially equivalent fixation to the bone. For example, the orthogonal or offset positioning of the screws can provide greater fixation over a shorter distance than a linear plate system illustrated in FIG. 8.

As illustrated in FIGS. 9A-9C, the multiplanar surgical plate system can utilize a first set of screws 922 implanted in a first direction and a second set of screws 923 implanted in a second direction. The first set of screws 922 as illustrated in FIGS. 9B-9C can be inserted in the z direction or into or out of the page. The second set of screws 923 can be inserted orthogonal to or perpendicular to the first set of screws 922 in the y direction as illustrated in FIGS. 9B-9C. The offset configuration of the screw placement in the bone can provide a more stable fixation and prevent movement of the device once implanted.

FIGS. 10A-10G illustrate embodiments of screw hole patterns of a multiplanar surgical plate. FIG. 10A illustrates a clover type pattern of screw holes on the fastening segments 1001 and 1002 and central segment 1003. The fastening segments 1001 and 1002 of the embodiments illustrated in FIGS. 10A-10G can be bent or curved to a 90 degree or substantially 90 degree angle for implantation and fixation for the bone. FIG. 10B illustrates an offset clover pattern of screw holes on the fastening segments 1001 and 1002 and the central segment 1003.

FIGS. 10C and 10D illustrate a barrel design of screw hole patterns shown in a linear plane, however, the design of FIG. 10C and 10D would form a barrel or semi-circular shape when the multiplanar plate is contoured or curved for implantation around the bone. The plate of FIGS. 10C and 10D have a fastening segment 1001 and a central segment 1003. The fastening segment 1001 of FIGS. 10C and 10D have one or more screw holes. FIG. 10D illustrates the barrel design of screw holes with an offset pattern. The offset pattern can minimize the stress at the junction or connection between the fastening segment and the central segment.

FIG. 10E illustrates an embodiment of a multiplanar surgical plate with a helix shape with fastening segments 1001 and 1002 and a central segment 1003. The screw holes of the segments can be distributed throughout the two segments as illustrated in FIG. 10E forming a helix shape fixation pattern.

FIG. 10F illustrates an embodiment of a multiplanar surgical plate with fastening segments 1001 and 1002 and a central segment 1003. The fastening segments 1001 and 1002 have arms and with screw holes. The central segment 1003 can have screw holes distributed throughout the length of the central segment as illustrated in FIG. 10F.

FIG. 10G illustrates an embodiment of a multiplanar surgical plate with a web shape with fastening segments 1001 and 1002 and a central segment 1003. The web shape can have various connecting portions 1004 connecting portions of the central segment 1003 with portions of the fastening segments 1001 and 1002 forming a web shaped device.

Figure 11:
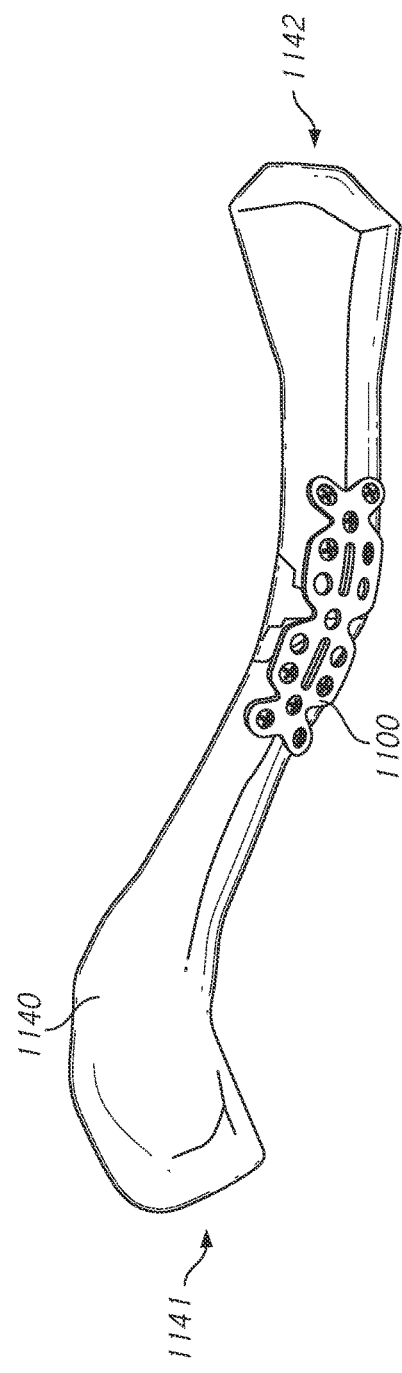
FIG. 11 illustrates an embodiment of a multiplanar surgical plate system positioned on a clavicle bone.

FIG. 11 illustrates an embodiment of a multiplanar surgical plate system positioned on a clavicle bone. FIG. 11 illustrates a posterior butterfly fracture in a clavicle bone. The clavicle bone 1140 illustrates the lateral 1141 and medial 1142 ends of the bone which aligns with the lateral and medial ends of the multiplanar surgical plate system 1100 as described herein. The multiplanar surgical plate system and the bone of FIG. 11 are used for illustrative purposes only and are not drawn to scale.

Figure 12:
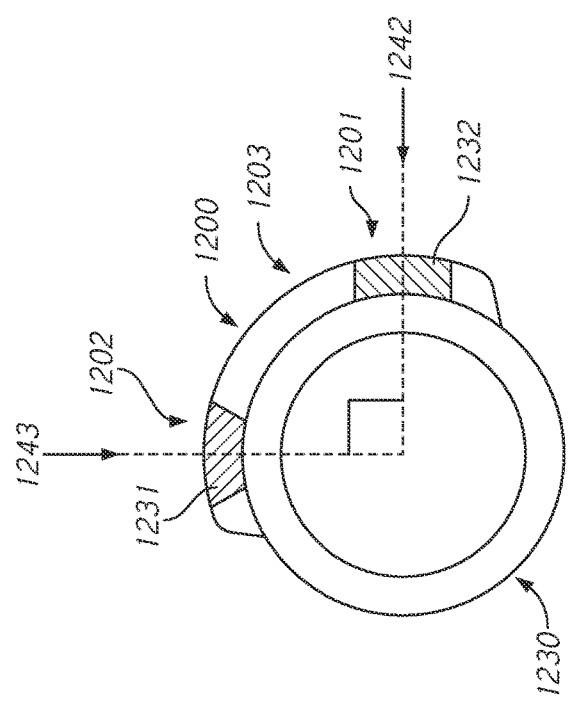
FIG. 12 illustrates a cross-sectional view of a bone and a multiplanar surgical plate system.

FIG. 12 illustrates a cross-sectional view of the clavicle bone 1230 and a multiplanar surgical plate system 1200. The multiplanar surgical plate can have fastening segments 1201 and 1202 and a central segment 1203. As illustrated in FIG. 12, the fastening segments 1201 and 1202 of the multiplanar surgical plate can be wrapped around at least two different surfaces of the bone. The two different surfaces of the bone can be orthogonal to each other. For example, the first fastening segment 1201 can be positioned on or adjacent to an anterior surface 1242 of the bone and the second fastening segment 1202 can be positioned on or adjacent to the superior surface 1243 of the bone. In such configuration, screws 1231 and 1232 can be inserted into the bone at the first and second fastening segments as illustrated in FIG. 12.

In such configuration, a first screw 1231 can be inserted at a superior surface 1243 and a second screw 1232 can be inserted into an anterior surface 1242. The screws 1231 and 1232 can be orthogonal or substantially orthogonal to each other. The orthogonal or substantially orthogonal orientation of the screws can provide a locked fixation for improved rotational control.

In some embodiments, additional screws and screw holes can be used in combination with the central segment and can be positioned at a 45 degree or substantially 45 degree angle to the screws 1231 in the first and second fastening segments. As illustrated in FIG. 12, the multiplanar surgical device can combine anterior and superior clavicle fixation into a single device. This can provide an orthogonal fixation, or in the range of "90-90" fixation, of the clavicle. In some embodiments, the fastening segments must contain minimum rotational distance separation to achieve optimal orthogonal fixation. In some embodiments, the edges of the device can be tapered (or distal edges with a smaller width than the more proximal portions of the device) to reduce irritation as described herein.

Figure 13:
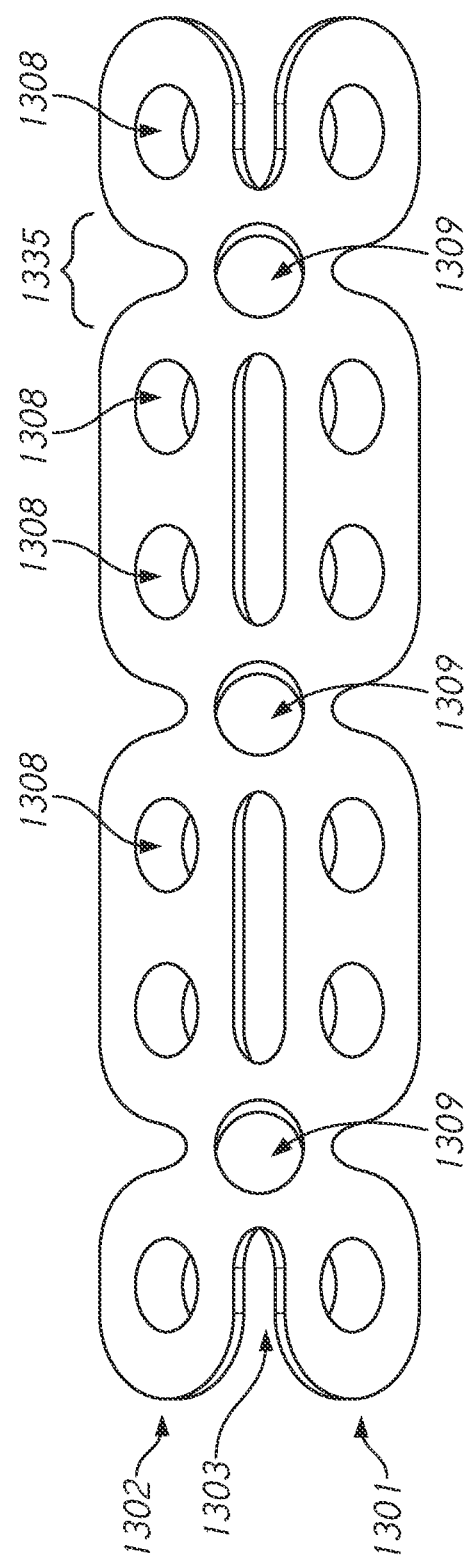
FIG. 13 illustrates an embodiment of a multiplanar surgical plate.

FIG. 13 illustrates an embodiment of a multiplanar surgical plate with fastening segments 1301 and 1302 and a central segment 1303. As illustrated in FIG. 13, the edges of the device can be rounded or curved to remove sharp edges from the plate. The multiplanar plate can have various screw holes 1308 to provide various options to lag fracture or compresses the fracture fragments together and gain fixation in the diaphysis or shaft of the bone.

In some embodiments, the central segment 1303 can include screw holes 1309. The screw holes 1309 can be used with non-locking screws to position the plate to allow an initial compression and contouring of the plate.

In some embodiments, the plate can have cutouts in the central portion and fastening segments to help with bending and contouring of the plate. For example, the fastening segment can have one or more cutouts 1335 which allow for contouring of the plate to the desired shape.

In some embodiments, the locking or compression screws used for fixation can range from 3.5 mm to 2.4 mm in diameter. In some embodiment, the plate and/or screw holes can be used to accommodate any type or size of screw. In some embodiments, drill diameters will range from 2.8 to 2.0 mm. In some embodiment, the plate, screws, and/or screw holes can be used to accommodate any type or size of drill diameters. Multiple screws of multiple different sizes can be used throughout the shorter horizontal length as described herein. The shorter length of the multiplanar device can allow for smaller incisions for implantation surgery.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:

1. A clavicle plate fixation system, the system comprising:
a plate sized for positioning on a clavicle bone, the plate comprising:
a first fastening segment, a second fastening segment, and a central segment, wherein the central segment connects the first and second fastening segment and the first fastening segment and the second fastening segment comprise one or more screw holes, wherein the plate comprises a longitudinal axis extending from a first end of the plate to a second end of the plate and passing through the central segment;
a first arm and a second arm positioned on the first fastening segment, wherein the first arm is on the first end of the plate and the second arm is on the second end of the plate; and
a third arm and a fourth arm positioned on the second fastening segment, wherein the third arm is on the first end of the plate and the fourth arm is on the second end of the plate;
wherein the first arm and the third arm are positioned on opposite sides of the longitudinal axis at the first end and the second arm and the fourth arm are positioned on opposite sides of the longitudinal axis at the second end;
wherein the first, second, third and fourth arms comprise a proximal end that connects to the central segment and a distal end comprises a screw hole; and
wherein the first fastening segment is offset from the second fastening segment at a first angle, wherein the first angle is between 45 degrees to 135 degrees.

2. The system of claim 1, wherein the first fastening segment is orthogonal to the second fastening segment.

3. The system of claim 1, wherein the central segment comprises one or more screw holes configured for bone fixation through the central segment.

4. The system of claim 1, wherein the first fastening segment comprises a first screw hole and the second fastening segment comprises a second screw hole; and the system further comprises a first screw and a second screw and wherein the first screw is configured to be positioned in the first screw hole and the second screw is configured to be positioned in the second screw hole.

5. The system of claim 4, wherein the first screw is configured to be inserted into the bone in a first direction and the second screw is configured to be inserted into the bone in a second direction and wherein the first direction is orthogonal to the second direction.

6. The system of claim 4, wherein the first screw is configured to be inserted into the bone in a first direction and the second screw is configured to be inserted into the bone in a second direction; wherein the first direction is offset from the second direction at a second angle, wherein the second angle is greater than 60 degrees.

7. The system of claim 1, a fifth arm positioned on the first fastening segment and a sixth arm positioned on the second fastening segment, wherein the fifth and sixth arms are positioned between the first end and the second end of the plate and are positioned on opposite sides of the longitudinal axis.

8. The system of claim 1, wherein the plate comprises a transverse axis transverse to the longitudinal axis, wherein the offset of the first fastening segment and the second fastening segment create a curvature in the plate, wherein the curvature in the transverse axis is not uniform.

9. The system of claim 4, wherein the first screw is configured to be inserted into the bone in a first direction and the second screw is configured to be inserted into the bone in a second direction; wherein the first direction is offset from the second direction at a second angle, wherein the first fastening segment is offset from the second segment, and wherein the second fastening segment is configured to be bent or curved along a width of the plate to adjust the second angle of the first screw with respect to the second screw.

10. The system of claim 1, wherein the central segment comprises one or more cut outs and one or more screw holes, wherein the one or more cutouts are configured to allow for bending and contouring of the plate.

11. The system of claim 7, wherein the central segment comprises one or more cutouts and one or more screw holes, wherein a first cutout is between the fifth and sixth arms.

12. The system of claim 1, wherein the first and second fastening segment are configured to secure the bone on at least two surfaces in at least two dimensions, wherein the surfaces comprise an anterior, posterior, superior, or inferior surfaces.

13. The system of claim 1, wherein the first, second, third, and fourth arms connect to the central segment at a connecting angle between 20 degrees to 160 degrees.

14. The system of claim 1, wherein the first fastening segment has a length extending from a distal most end of the first arm to a distal most end of the second arm, wherein the length of the first fastening segment is greater than the length of the central segment.

15. A clavicle plate fixation system, the system comprising:
a plate sized for positioning on a clavicle bone, the plate comprising:
a first fastening segment, a second fastening segment, and a central segment, wherein the central segment connects the first and second fastening segment, wherein the first fastening segment, the second fastening segment, and the central segment each comprise one or more screw holes, and wherein the plate comprises a first, medial end and a second, lateral end;
the first fastening segment comprising a portion on the first, medial end of the plate comprising a first screw hole and the second fastening segment comprising a portion on the second, lateral end of the plate comprising a second screw hole; wherein the first fastening segment and the second fastening segment are positioned on opposite sides of a longitudinal axis extending through the central segment; and
wherein the first screw hole on the first fastening segment is offset from the second screw hole on the second fastening segment at a first angle, wherein the first angle is between 45 degrees to 135 degrees.

16. The system of claim 15, wherein the central segment comprises a plurality of screw holes, wherein the plurality of screw holes are aligned in a single row that extends along the central segment between the first screw hole on the first, medial end of the plate and the second screw hole on the second, lateral end of the plate.

17. The system of claim 15, wherein the first and second screw holes on the first and second fastening segments are configured to receive a screw and secure the bone on at least two surfaces in at least two dimensions, wherein the surfaces comprise an anterior, posterior, superior, or inferior surfaces.

18. The system of claim 15, wherein the portion of the first fastening segment comprising the first screw hole aligns with a first plane, the portion of the second fastening segment comprising the second screw hole aligns with a second plane, and the central segment comprises a third screw hole aligned with a third plane.

19. The system of claim 18, wherein the first plane is an anterior or posterior plane and the second plane is an inferior or superior plane.

20. The system of claim 18, wherein the system further comprises a first screw and a second screw and wherein the first screw is configured to be inserted into the first screw hole perpendicular to the first plane and the second screw is configured to be inserted into the second screw hole perpendicular to the second plane.

21. The system of claim 20, wherein the first screw is configured to be inserted into the bone in a first direction and the second screw is configured to be inserted into the bone in a second direction and wherein the first direction is orthogonal to the second direction.

* * * * *